(12) United States Patent
Shibata et al.

(10) Patent No.: US 8,703,969 B2
(45) Date of Patent: Apr. 22, 2014

(54) TRIFLUOROMETHYLTHIOPHENIUM DERIVATIVE SALT, METHOD FOR PRODUCING THE SAME, AND METHOD FOR PRODUCING TRIFLUOROMETHYL-CONTAINING COMPOUNDS USING THE SAME

(75) Inventors: Norio Shibata, Aichi (JP); Takumi Kagawa, Yamaguchi (JP)

(73) Assignees: Nagoya Institute of Technology, Aichi (JP); Tosoh F-Tech, Inc., Yamaguchi (JP)

( * ) Notice: Subject to any disclaimer, the term of this patent is extended or adjusted under 35 U.S.C. 154(b) by 43 days.

(21) Appl. No.: 13/378,420

(22) PCT Filed: Jul. 13, 2010

(86) PCT No.: PCT/JP2010/004518
§ 371 (c)(1),
(2), (4) Date: Feb. 9, 2012

(87) PCT Pub. No.: WO2011/013307
PCT Pub. Date: Feb. 3, 2011

(65) Prior Publication Data
US 2012/0130090 A1  May 24, 2012

(30) Foreign Application Priority Data
Jul. 28, 2009 (JP) ................................ 2009-174930

(51) Int. Cl.
C07D 333/54 (2006.01)
C07C 321/28 (2006.01)

(52) U.S. Cl.
CPC ............ *C07D 333/54* (2013.01); *C07C 321/28* (2013.01)
USPC ............................................. 549/49; 568/56

(58) Field of Classification Search
CPC .................................................... C07D 333/54
See application file for complete search history.

(56) References Cited

U.S. PATENT DOCUMENTS

2004/0023806 A1* 2/2004 Ziegler et al. ................ 504/244

FOREIGN PATENT DOCUMENTS

| JP | 3-197479 | 8/1991 |
|---|---|---|
| JP | 2010-120867 | 6/2010 |
| JP | 2010120867 | * 6/2010 |
| WO | 99/06389 | 2/1999 |

OTHER PUBLICATIONS

International Search Report issued Aug. 24, 2010 in International (PCT) Application No. PCT/JP2010/004518, of which the present application is the national stage.

S. Noritake et al., "Fusei Trifluoromethyl-ka Hanno no Kaihatsu Kenkyu", 89th Annual Meeting of Chemical Society of Japan in Spring (2009) Koen Yokoshu II, p. 1128 (Yoko No. 1 G2-35), 2009.
S. Noritake et al., "Fluorinated Johnson Reagent for Transfer-Trifluoromethylation to Carbon Nucleophiles", European Journal of Organic Chemistry, pp. 3465-3468, 2008.
A. Matsnev et al., "Efficient Access to Extended Yagupolskii-Umemoto-Type Reagents: Triflic Acid Catalyzed Intramolecular Cyclization of *ortho*-Ethynylaryltrifluoromethylsulfanes", Angew. Chem. Int. Ed., 49, pp. 572-576, 2010.
T. Shibata et al., "Kyundenshiteki Trifluoromethyl-ka Shiyaku no Sosei to Shin Tenkai", Kagaku Kogyo, 61, (4), pp. 265-281, 2010.
L. M. Yagupol'skii et al., Fluoro(trifluoromethyl)arylsulfonium and (Trifluoromethyl)-Diarylsulfonium Salts, pp. 103-106, Institute of Organic Chemistry, Academy of Sciences of the Ukrainian SSR, Keiv., translated from Zhurnal Organicheskoi Khimmi, vol. 20, No. 1, pp. 115-118, Jan. 1984.
International Preliminary Report on Patentability with Written Opinion issued Feb. 7, 2012 in International (PCT) Application No. PCT/JP2010/004518.

* cited by examiner

*Primary Examiner* — Noble Jarrell
*Assistant Examiner* — Valerie Rodriguez-Garcia
(74) *Attorney, Agent, or Firm* — Wenderoth, Lind & Ponack, L.L.P.

(57) ABSTRACT

A trifluoromethylthiophenium derivative salt useful as synthetic intermediates for pharmaceuticals and agrochemicals, a method for producing the same, and a method for producing trifluoromethyl-containing compounds using the same are provided. An S-(trifluoromethyl)-benzo[b]thiophenium derivative salt is represented by the following general formula (1):

[Chemical formula 1]

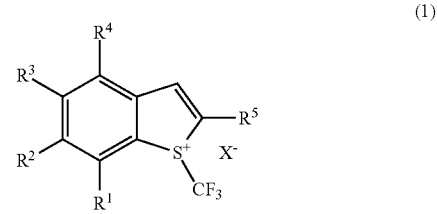

wherein $R^1$, $R^2$, $R^3$, and $R^4$ are each independently a hydrogen atom, a methyl group, an ethyl group, a linear, branched, or cyclic alkyl group having 3 to 10 carbon atoms, a methoxy group, an ethoxy group, a linear, branched, or cyclic alkyloxy group having 3 to 10 carbon atoms, a fluorine atom, a chlorine atom, a bromine atom, a nitro group, or a cyano group, $R^5$ is a methyl group, an ethyl group, a linear, branched, or cyclic alkyl group having 3 to 10 carbon atoms, a phenyl group, or a substituted phenyl group, and $X^-$ represents an anion. Various trifluoromethyl-containing compounds are produced using a method for producing the S-(trifluoromethyl)-benzo[b]thiophenium derivative salt, and using the S-(trifluoromethyl)-benzo[b]thiophenium derivative salt as a trifluoromethylating agent.

9 Claims, No Drawings

TRIFLUOROMETHYLTHIOPHENIUM DERIVATIVE SALT, METHOD FOR PRODUCING THE SAME, AND METHOD FOR PRODUCING TRIFLUOROMETHYL-CONTAINING COMPOUNDS USING THE SAME

TECHNICAL FIELD

The present invention relates to a novel trifluoromethylthiophenium derivative salt, a method for producing the same, an intermediate thereof, and a method for producing trifluoromethyl-containing compounds using the same. The trifluoromethyl-containing compounds are useful as synthetic intermediates for pharmaceuticals and agrochemicals.

BACKGROUND ART

The trifluoromethylthiophenium derivative salt of the present invention has not been known. As the conventional technique about a trifluoromethylating agent, 4-chlorophenyl-2',4'-dimethylphenyl(trifluoromethyl)sulfonium hexafluoroantimonate (Non-Patent Literature 1), (trifluoromethyl)dibenzonium salts (Patent Literatures 1 and 2), and the like have been known.

CITATION LIST

Patent Literature

Patent Literature 1: Japanese Patent No. 2918598
Patent Literature 2: International Publication No. WO99/06389 pamphlet

Non-Patent Literature

Non-Patent Literature 1: J. Org. Chem. USSR, 20, 103 (1984)

SUMMARY OF INVENTION

Technical Problem

With regard to the compounds described in Non-Patent Literature 1, there have been problems of a long production process and use of highly toxic tetrafluorosulfur, antimony pentafluoride, or the like as one of raw materials.

On the other hand, in manufacturing of the compounds described in Patent Literatures 1 and 2, fluorine gas which is highly toxic and difficult to handling to be used. In order to avoid this, although other methods using peroxides having a high risk have been proposed, such methods cannot be said to be industrially applied.

The present invention is to propose a novel trifluoromethylating agent which can be industrially produced, a method for producing the same, and a trifluoromethylation reaction using the same.

Solution to Problem

The present inventor has intensively studied a method for solving the above-described problems, found a novel S-(trifluoromethyl)-benzo[b]thiophenium derivative salt, and found that the compound can be easily produced at a high yield. Further, the inventor has found that the obtained S-(trifluoromethyl)-benzo[b]thiophenium derivative salt is useful as a trifluoromethylating agent, and can be used to trifluoromethylate various compounds, leading to the completion of the present invention.

That is to say, the present invention relates to an S-(trifluoromethyl)-benzo[b]thiophenium derivative salt represented below, a method for producing the same, an intermediate thereof, and a method for producing trifluoromethyl-containing compounds using the same.

Accordingly, the present invention provides:

[Section 1] An S-(trifluoromethyl)-benzo[b]thiophenium derivative salt represented by the following general formula (1),

[Chemical formula 1]

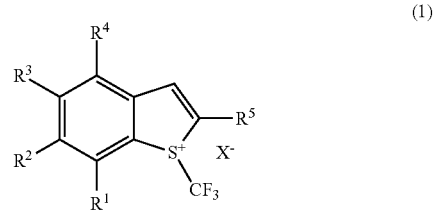

(1)

wherein $R^1$, $R^2$, $R^3$, and $R^4$ each independently represent a hydrogen atom, a methyl group, an ethyl group, a linear, branched, or cyclic alkyl group having 3 to 10 carbon atoms, a methoxy group, an ethoxy group, a linear, branched, or cyclic alkyloxy group having 3 to 10 carbon atoms, a fluorine atom, a chlorine atom, a bromine atom, a nitro group, or a cyano group, $R^5$ is a methyl group, an ethyl group, a linear, branched, or cyclic alkyl group having 3 to 10 carbon atoms, a phenyl group, or a substituted phenyl group, and $X^-$ represents an anion.

[Section 2] The S-(trifluoromethyl)-benzo[b]thiophenium derivative salt described in section 1, characterized in that in the above general formula (1), $R^1$, $R^2$, $R^3$, and $R^4$ are all hydrogen atoms, $R^5$ is a cyclic alkyl group having 3 to 7 carbon atoms, and $X^-$ is a trifluoromethanesulfonate ion or a tetrafluoroborate ion.

[Section 3] The S-(trifluoromethyl)-benzo[b]thiophenium derivative salt described in section 1 or 2, characterized in that in the above general formula (1), $R^5$ is a cyclopropyl group.

[Section 4] A (trifluoromethyl)-(2-ethynyl)phenyl sulfide derivative represented by the following general formula (2),

[Chemical formula 2]

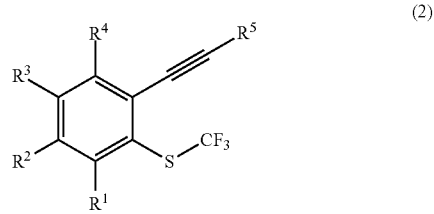

(2)

wherein $R^1$, $R^2$, $R^3$, $R^4$, and $R^5$ are as defined above.

[Section 5] The (trifluoromethyl)-(2-ethynylphenyl)sulfide derivative described in section 4, characterized in that in the above general formula (2), $R^1$, $R^2$, $R^3$, and $R^4$ are all hydrogen atoms, $R^5$ is a cyclic alkyl group having 3 to 7 carbon atoms, and $X^-$ is a trifluoromethanesulfonate ion or a tetrafluoroborate ion.

[Section 6] The (trifluoromethyl)-(2-ethynylphenyl)sulfide derivative described in section 4 or 5, characterized in that in the above general formula (2), $R^5$ is a cyclopropyl group.

[Section 7] A method for producing the S-(trifluoromethyl)-benzo[b]thiophenium derivative salt represented by the above general formula (1) described in section 1, characterized by including reacting the (trifluoromethyl)-(2-ethynylphenyl)sulfide derivative represented by the above general formula (2) described in section 4 with an acid.

[Section 8] A method for producing the S-(trifluoromethyl)-benzo[b]thiophenium derivative salt represented by the above general formula (1) described in section 2, characterized by including reacting the (trifluoromethyl)-(2-ethynylphenyl)sulfide derivative represented by the above general formula (2) described in section 5 with an acid.

[Section 9] A method for producing the S-(trifluoromethyl)-benzo[b]thiophenium derivative salt represented by the above general formula (1) described in section 3, characterized by including reacting the (trifluoromethyl)-(2-ethynylphenyl)sulfide derivative represented by the above general formula (2) described in section 6 with an acid.

[Section 10] A trifluoromethylating agent including the S-(trifluoromethyl)-benzo[b]thiophenium derivative salt represented by the above general formula (1) described in section 1, 2, or 3.

[Section 11] A method for producing an α-trifluoromethylcarboxylic acid derivative represented by the following general formula (4),

[Chemical formula 4]

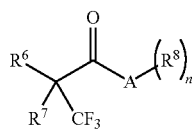

(4)

wherein $R^6$, $R^7$, $R^8$, A, and n are as defined below, the method characterized by including reacting the trifluoromethylating agent described in section 10 with a carboxylic acid derivative represented by the following general formula (3)

[Chemical formula 3]

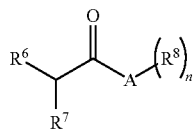

(3)

wherein $R^6$ and $R^7$ each independently represent a hydrogen atom, a methyl group, an ethyl group, a linear, branched, or cyclic alkyl group having 3 to 10 carbon atoms, a phenyl group, a substituted phenyl group, a benzyl group, or a phenylethyl group, $R^8$ is a methyl group, an ethyl group, a n-propyl group, an iso-propyl group, a n-butyl group, an iso-butyl group, a tert-butyl group, a phenyl group, a substituted phenyl group, or a benzyl group. Further, $R^6$ and $R^7$ may be condensed to form a 3 to 8-membered ring, or may contain a carbonyl group. A represents a nitrogen atom or an oxygen atom, n represents 1 when A is an oxygen atom, or n represents 2 when A is a nitrogen atom.

[Section 12] A method for producing a trifluoromethylated malononitrile derivative represented by the following general formula (6),

[Chemical formula 6]

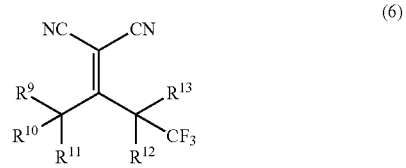

(6)

wherein $R^9$, $R^{10}$, $R^{11}$, $R^{12}$, and $R^{13}$ are as defined below or the following general formula (7),

[Chemical Formula 7]

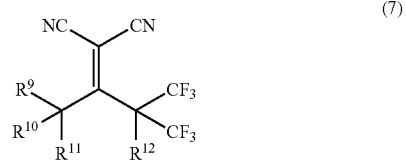

(7)

wherein $R^9$, $R^{10}$, $R^{11}$, and $R^{12}$ are as defined below, the method characterized by including reacting the trifluoromethylating agent described in section 10 with a malononitrile derivative represented by the following general formula (5),

[Chemical formula 5]

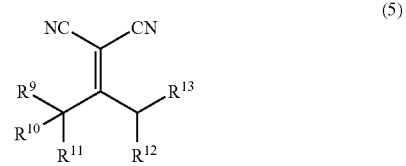

(5)

wherein $R^9$, $R^{10}$, $R^{11}$, $R^{12}$, and $R^{13}$ each independently represent a hydrogen atom, a methyl group, an ethyl group, a linear, branched, or cyclic alkyl group having 3 to 10 carbon atoms, a phenyl group, a substituted phenyl group, or a naphthyl group, $R^9$, $R^{10}$, and $R^{11}$ may form an aromatic ring or a substituted aromatic ring, or $R^{11}$ and $R^{12}$ may be condensed to form a 4 to 7-membered ring, and provided that $R^9$, $R^{10}$, $R^{11}$, $R^{12}$, and $R^{13}$ are not all hydrogen atoms.

Advantageous Effects of Invention

The present invention proposes the novel trifluoromethylating agent useful as synthetic intermediates for pharmaceuticals and agrochemicals, the method for producing the same, and trifluoromethylation reaction using the same.

DESCRIPTION OF EMBODIMENTS

Hereinafter, the present invention will be described in detail.

In the present invention, examples of the linear, branched, or cyclic alkyl group having 3 to 10 carbon atoms include a n-propyl group, an iso-propyl group, a cyclopropyl group, a n-butyl group, a sec-butyl group, a tert-butyl group, a cyclobutyl group, a n-pentyl group, a cyclopentyl group, a n-hexyl group, a cyclohexyl group, a n-heptyl group, a cycloheptyl group, a n-octyl group, a cyclooctyl group, a n-nonyl group, a cyclononyl group, a n-decyl group, a cyclodecyl group, and the like.

In the present invention, examples of the linear, branched, or cyclic alkyloxy group having 3 to 10 carbon atoms include a n-propoxy group, an iso-propoxy group, a cyclopropoxy group, a n-butoxy group, a sec-butoxy group, a tert-butoxy group, a cyclobutoxy group, a n-pentoxy group, a cyclopentoxy group, a n-hexyloxy group, a cyclohexyloxy group, a n-heptyloxy group, a cycloheptyloxy group, a n-octyloxy group, a cyclooctyloxy group, a n-nonyloxy group, a cyclononyloxy group, a n-decyloxy group, a cyclodecyloxy group, and the like.

In the present invention, examples of the substituted phenyl group include a 2-methylphenyl group, a 3-methylphenyl group, a 4-methylphenyl group, a 2-ethylphenyl group, a 3-ethylphenyl group, a 4-ethylphenyl group, a 2-n-propylphenyl group, a 3-n-propylphenyl group, a 4-n-propylphenyl group, a 2-iso-propylphenyl group, a 3-iso-propylphenyl group, a 4-iso-propylphenyl group, a 2-n-butylphenyl group, a 3-n-butylphenyl group, a 4-n-butylphenyl group, a 2-sec-butylphenyl group, a 3-sec-butylphenyl group, a 4-sec-butylphenyl group, a 2-tert-butylphenyl group, a 3-tert-butylphenyl group, a 4-tert-butylphenyl group, a 4-n-pentylphenyl group, a 4-n-hexylphenyl group, a 4-n-heptylphenyl group, a 4-n-octylphenyl group, a 4-n-nonylphenyl group, a 4-n-decylphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxyphenyl group, a 3-n-propoxyphenyl group, a 4-n-propoxyphenyl group, a 2-iso-propoxyphenyl group, a 3-iso-propoxyphenyl group, a 4-iso-propoxyphenyl group, a 2-n-butoxyphenyl group, a 3-n-butoxyphenyl group, a 4-n-butoxyphenyl group, a 2-sec-butoxyphenyl group, a 3-sec-butoxyphenyl group, a 4-sec-butoxyphenyl group, a 2-tert-butoxyphenyl group, a 3-tert-butoxyphenyl group, a 4-tert-butoxyphenyl group, a 4-n-pentoxyphenyl group, a 4-n-hexyloxyphenyl group, a 4-n-heptyloxyphenyl group, a 4-n-octyloxyphenyl group, a 4-n-nonyloxyphenyl group, a 4-n-decyloxyphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, and the like.

In the present invention, examples of the aromatic ring or substituted aromatic ring include a phenyl group, a 2-methylphenyl group, a 3-methylphenyl group, a 4-methylphenyl group, a 2-ethylphenyl group, a 3-ethylphenyl group, a 4-ethylphenyl group, a 2-n-propylphenyl group, a 3-n-propylphenyl group, a 4-n-propylphenyl group, a 2-iso-propylphenyl group, a 3-iso-propylphenyl group, a 4-iso-propylphenyl group, a 2-n-butylphenyl group, a 3-n-butylphenyl group, a 4-n-butylphenyl group, a 2-sec-butylphenyl group, a 3-sec-butylphenyl group, a 4-sec-butylphenyl group, a 2-tert-butylphenyl group, a 3-tert-butylphenyl group, a 4-tert-butylphenyl group, a 4-n-pentylphenyl group, a 4-n-hexylphenyl group, a 4-n-heptylphenyl group, a 4-n-octylphenyl group, a 4-n-nonylphenyl group, a 4-n-decylphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxyphenyl group, a 3-n-propoxyphenyl group, a 4-n-propoxyphenyl group, a 2-iso-propoxyphenyl group, a 3-iso-propoxyphenyl group, a 4-iso-propoxyphenyl group, a 2-n-butoxyphenyl group, a 3-n-butoxyphenyl group, a 4-n-butoxyphenyl group, a 2-sec-butoxyphenyl group, a 3-sec-butoxyphenyl group, a 4-sec-butoxyphenyl group, a 2-tert-butoxyphenyl group, a 3-tert-butoxyphenyl group, a 4-tert-butoxyphenyl group, a 4-n-pentoxyphenyl group, a 4-n-hexyloxyphenyl group, a 4-n-heptyloxyphenyl group, a 4-n-octyloxyphenyl group, a 4-n-nonyloxyphenyl group, a 4-n-decyloxyphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-cyanophenyl group, a 3-cyanophenyl group, a 4-cyanophenyl group, a 2-nitrophenyl group, a 3-nitrophenyl group, a 4-nitrophenyl group, an indan-1-yl group, an indan-2-yl group, a 5-methylindan-1-yl group, a 5-methylindan-2-yl group, a 5-methoxyindan-1-yl group, a 5-methoxyindan-2-yl group, a 5-fluoroindan-1-yl group, a 5-fluoroindan-2-yl group, a 5-chloroindan-1-yl group, a 5-chloroindan-2-yl group, a 5-bromoindan-1-yl group, a 5-bromoindan-2-yl group, a 3,4-dihydro-1(2H)-naphthalen-1-yl group, a 3,4-dihydro-1(2H)-naphthalen-2-yl group, a 6-methyl-3,4-dihydro-1(2H)-naphthalen-1-yl group, a 6-methyl-3,4-dihydro-1(2H)-naphthalen-2-yl group, a 6-methoxy-3,4-dihydro-1(2H)-naphthalen-1-yl group, a 6-methoxy-3,4-dihydro-1(2H)-naphthalen-2-yl group, a 6-fluorol-3,4-dihydro-1(2H)-naphthalen-1-yl group, a 6-fluorol-3,4-dihydro-1(2H)-naphthalen-2-yl group, a 6-chloro-3,4-dihydro-1(2H)-naphthalen-1-yl group, a 6-chloro-3,4-dihydro-1(2H)-naphthalen-2-yl group, a 6-bromo-3,4-dihydro-1(2H)-naphthalen-1-yl group, a 6-bromo-3,4-dihydro-1(2H)-naphthalen-2-yl group, and the like.

Examples of the anion represented by $X^-$ in the present invention include a fluorine ion, a chlorine ion, a bromine ion, an iodine ion, a perchlorate ion, a perbromate ion, a periodate ion, a cyano ion, a hydrogensulfate ion, an acetate ion, a trifluoroacetate ion, a methanesulfonate ion, a trifluoromethansulfonate ion, a tetrafluoroborate ion, and the like.

The S-(trifluoromethyl)-benzo[b]thiophenium derivative salt of the present invention represented by the above general formula (1) can be prepared by reaction of a (trifluoromethyl)-(2-ethynylphenyl)sulfide derivative represented by the above general formula (2) with an acid. Examples of acids applicable to production of the S-(trifluoromethyl)-benzo[b]thiophenium derivative salt of the present invention represented by the general formula (1) include hydrofluoric acid, hydrochloric acid, hydrobromic acid, hydroiodic acid, perchloric acid, perbromic acid, periodic acid, hydrogen cyanide, sulfuric acid, acetic acid, trifluoroacetic acid, methansulfonic acid, trifluoromethanesulfonic acid, and tetrafluoroboric acid, and the acid is preferably trifluoromethanesulfonic acid or tetrafluoroboric acid.

Specific examples of the S-(trifluoromethyl)-benzo[b]thiophenium derivative salt of the present invention represented by the above general formula (1) include S-(trifluoromethyl)-2-methylbenzo[b]thiophenium fluolid, S-(trifluoromethyl)-2-methylbenzo[b]thiophenium chloride, S-(trifluoromethyl)-2-methylbenzo[b]thiophenium bromide, S-(trifluoromethyl)-2-methylbenzo[b]thiophenium iodide, S-(trifluoromethyl)-2-methylbenzo[b]thiophenium perchlorate, S-(trifluoromethyl)-2-methylbenzo[b]thiophenium perbromate, S-(trifluoromethyl)-2-methylbenzo[b]thiophenium periodate, S-(trifluoromethyl)-2-methylbenzo[b]thiophenium cyanide, S-(trifluoromethyl)-2-methylbenzo[b]thiophenium hydrogensulfate, S-(trifluoromethyl)-2-methylbenzo[b]thiophenium acetate, S-(trifluoromethyl)-2-methylbenzo[b]thiophenium trifluoroacetate, S-(trifluoromethyl)-2-methylbenzo[b]thiophenium methanesulfonate, S-(trifluoromethyl)-2-methylbenzo[b]thiophenium trifluoromethanesulfonate, S-(trifluoromethyl)-2-methylbenzo[b]thiophenium tetrafluoroborate, S-(trifluoromethyl)-2-ethylbenzo[b]thiophenium fluolid, S-(trifluoromethyl)-2-ethylbenzo[b]thiophenium chloride, S-(trifluoromethyl)-2-ethylbenzo[b]thiophenium bromide, S-(trifluoromethyl)-2-ethylbenzo[b]thiophenium iodide, S-(trifluoromethyl)-2-ethylbenzo[b]thiophenium perchlorate, S-(trifluoromethyl)-2-ethylbenzo[b]thiophenium perbromate, S-(trifluoromethyl)-2-ethylbenzo[b]thiophenium periodate, S-(trifluoromethyl)-2-ethylbenzo[b]thiophenium cyanide, S-(trifluoromethyl)-2-ethylbenzo[b]thiophenium hydrogensulfate, S-(trifluoromethyl)-2-ethylbenzo[b]thiophenium acetate, S-(trifluoromethyl)-2-ethylbenzo[b]thiophenium trifluoroacetate, S-(trifluoromethyl)-2-ethylbenzo[b]thiophenium methanesulfonate, S-(trifluoromethyl)-2-ethylbenzo[b]thiophenium trifluoromethanesulfonate, S-(trifluoromethyl)-2-ethylbenzo[b]thiophenium tetrafluoroborate, S-(trifluoromethyl)-2-n-propylbenzo[b]thiophenium fluolid, S-(trifluoromethyl)-2-n-propylbenzo[b]thiophenium chloride, S-(trifluoromethyl)-2-n-propylbenzo[b]thiophenium bromide, S-(trifluoromethyl)-2-n-propylbenzo[b]thiophenium iodide, S-(trifluoromethyl)-2-n-propylbenzo[b]thiophenium perchlorate, S-(trifluoromethyl)-2-n-propylbenzo[b]thiophenium perbromate, S-(trifluoromethyl)-2-n-propylbenzo[b]thiophenium periodate, S-(trifluoromethyl)-2-n-propylbenzo[b]thiophenium cyanide, S-(trifluoromethyl)-2-n-propylbenzo[b]thiophenium hydrogensulfate, S-(trifluoromethyl)-2-n-propylbenzo[b]thiophenium acetate, S-(trifluoromethyl)-2-n-propylbenzo[b]thiophenium trifluoroacetate, S-(trifluoromethyl)-2-n-propylbenzo[b]thiophenium methanesulfonate, S-(trifluoromethyl)-2-n-propylbenzo[b]thiophenium trifluoromethanesulfonate, S-(trifluoromethyl)-2-n-propylbenzo[b]thiophenium tetrafluoroborate, S-(trifluoromethyl)-2-iso-propylbenzo[b]thiophenium fluolid, S-(trifluoromethyl)-2-iso-propylbenzo[b]thiophenium chloride, S-(trifluoromethyl)-2-iso-propylbenzo[b]thiophenium bromide, S-(trifluoromethyl)-2-iso-propylbenzo[b]thiophenium iodide, S-(trifluoromethyl)-2-iso-propylbenzo[b]thiophenium perchlorate, S-(trifluoromethyl)-2-iso-propylbenzo[b]thiophenium perbromate, S-(trifluoromethyl)-2-iso-propylbenzo[b]thiophenium periodate, S-(trifluoromethyl)-2-iso-propylbenzo[b]thiophenium cyanide, S-(trifluoromethyl)-2-iso-propylbenzo[b]thiophenium hydrogensulfate, S-(trifluoromethyl)-2-iso-propylbenzo[b]thiophenium acetate, S-(trifluoromethyl)-2-iso-propylbenzo[b]thiophenium trifluoroacetate, S-(trifluoromethyl)-2-iso-propylbenzo[b]thiophenium methanesulfonate, S-(trifluoromethyl)-2-iso-propylbenzo[b]thiophenium trifluoromethanesulfonate, S-(trifluoromethyl)-2-iso-propylbenzo[b]thiophenium tetrafluoroborate, S-(trifluoromethyl)-2-cyclopropylbenzo[b]thiophenium fluolid, S-(trifluoromethyl)-2-cyclopropylbenzo[b]thiophenium chloride, S-(trifluoromethyl)-2-cyclopropylbenzo[b]thiophenium bromide, S-(trifluoromethyl)-2-cyclopropylbenzo[b]thiophenium iodide, S-(trifluoromethyl)-2-cyclopropylbenzo[b]thiophenium perchlorate, S-(trifluoromethyl)-2-cyclopropylbenzo[b]thiopheniumperbromate, S-(trifluoromethyl)-2-cyclopropylbenzo[b]thiophenium periodate, S-(trifluoromethyl)-2-cyclopropylbenzo[b]thiophenium cyanide, S-(trifluoromethyl)-2-cyclopropylbenzo[b]thiophenium hydrogensulfate, S-(trifluoromethyl)-2-cyclopropylbenzo[b]thiophenium acetate, S-(trifluoromethyl)-2-cyclopropylbenzo[b]thiophenium trifluoroacetate, S-(trifluoromethyl)-2-cyclopropylbenzo[b]thiophenium methanesulfonate, S-(trifluoromethyl)-2-cyclopropylbenzo[b]thiophenium trifluoromethanesulfonate, S-(trifluoromethyl)-2-cyclopropylbenzo[b]thiophenium tetrafluoroborate, S-(trifluoromethyl)-2-n-butylbenzo[b]thiophenium fluolid, S-(trifluoromethyl)-2-n-butylbenzo[b]thiophenium chloride, S-(trifluoromethyl)-2-n-butylbenzo[b]thiophenium bromide, S-(trifluoromethyl)-2-n-butylbenzo[b]thiophenium iodide, S-(trifluoromethyl)-2-n-butylbenzo[b]thiophenium perchlorate, S-(trifluoromethyl)-2-n-butylbenzo[b]thiophenium perbromate, S-(trifluoromethyl)-2-n-butylbenzo[b]thiophenium periodate, S-(trifluoromethyl)-2-n-butylbenzo[b]thiophenium cyanide, S-(trifluoromethyl)-2-n-butylbenzo[b]thiophenium hydrogensulfate, S-(trifluoromethyl)-2-n-butylbenzo[b]thiophenium acetate, S-(trifluoromethyl)-2-n-butylbenzo[b]thiophenium trifluoroacetate, S-(trifluoromethyl)-2-n-butylbenzo[b]thiophenium methanesulfonate, S-(trifluoromethyl)-2-n-butylbenzo[b]thiophenium trifluoromethanesulfonate, S-(trifluoromethyl)-2-n-butylbenzo[b]thiophenium tetrafluoroborate, S-(trifluoromethyl)-2-iso-butylbenzo[b]thiophenium fluolid, S-(trifluoromethyl)-2-iso-butylbenzo[b]thiophenium chloride, S-(trifluoromethyl)-2-iso-butylbenzo[b]thiophenium bromide, S-(trifluoromethyl)-2-iso-butylbenzo[b]thiophenium iodide, S-(trifluoromethyl)-2-iso-butylbenzo[b]thiophenium perchlorate, S-(trifluoromethyl)-2-iso-butylbenzo[b]thiophenium perbromate, S-(trifluoromethyl)-2-iso-butylbenzo[b]thiophenium periodate, S-(trifluoromethyl)-2-iso-butylbenzo[b]thiophenium cyanide, S-(trifluoromethyl)-2-iso-butylbenzo[b]thiophenium hydrogensulfate, S-(trifluoromethyl)-2-iso-butylbenzo[b]thiophenium acetate, S-(trifluoromethyl)-2-iso-butylbenzo[b]thiophenium trifluoroacetate, S-(trifluoromethyl)-2-iso-butylbenzo[b]thiophenium methanesulfonate, S-(trifluoromethyl)-2-iso-butylbenzo[b]thiophenium trifluoromethanesulfonate, S-(trifluoromethyl)-2-iso-butylbenzo[b]thiophenium tetrafluoroborate, S-(trifluoromethyl)-2-tert-butylbenzo[b]thiophenium fluolid, S-(trifluoromethyl)-2-tert-butylbenzo[b]thiophenium chloride, S-(trifluoromethyl)-2-tert-butylbenzo[b]thiophenium bromide, S-(trifluoromethyl)-2-tert-butylbenzo[b]thiophenium iodide, S-(trifluoromethyl)-2-tert-butylbenzo[b]thiophenium perchlorate, S-(trifluoromethyl)-2-tert-butylbenzo[b]thiophenium perbromate, S-(trifluoromethyl)-2-tert-butylbenzo[b]thiophenium periodate, S-(trifluoromethyl)-2-tert-butylbenzo[b]thiophenium cyanide, S-(trifluoromethyl)-2-tert-butylbenzo[b]thiophenium hydrogensulfate, S-(trifluoromethyl)-2-tert-butylbenzo[b]thiophenium acetate, S-(trifluoromethyl)-2-tert-butylbenzo[b]thiophenium trifluoroacetate, S-(trifluoromethyl)-2-tert-butylbenzo[b]thiophenium methanesulfonate, S-(trifluoromethyl)-2-tert-butylbenzo[b]thiophenium trifluoromethanesulfonate, S-(trifluoromethyl)-2-tert-butylbenzo[b]thiophenium tetrafluoroborate, S-(trifluoromethyl)-2-n-butylbenzo[b]thiophenium fluolid, S-(trifluoromethyl)-2-n-butylbenzo[b]thiophenium chloride, S-(trifluoromethyl)-2-n-butylbenzo[b]thiophenium bromide, S-(trifluoromethyl)-2-n-butylbenzo[b]thiophenium iodide, S-(trifluoromethyl)-2-n-butylbenzo[b]thiophenium perchlorate, S-(trifluoromethyl)-2-n-butylbenzo[b]thiophenium perbromate, S-(trifluoromethyl)-2-n-butylbenzo[b]thiophenium periodate, S-(trifluoromethyl)-2-n-butylbenzo[b]thiophenium cyanide, S-(trifluoromethyl)-2-n-butylbenzo[b]thiophenium hydrogensulfate, S-(trifluoromethyl)-2-n-butylbenzo[b]thiophenium acetate, S-(trifluoromethyl)-2-n-butylbenzo[b]thiophenium trifluoroacetate, S-(trifluoromethyl)-2-n-butylbenzo[b]thiophenium methanesulfonate, S-(trifluoromethyl)-2-n-butylbenzo[b]thiophenium trifluoromethanesulfonate, S-(trifluoromethyl)-2-n-butylbenzo[b]thiophenium tetrafluoroborate, S-(trifluoromethyl)-2-cyclobutylbenzo[b]thiophenium fluolid, S-(trifluoromethyl)-2-cyclobutylbenzo[b]thiophenium chloride, S-(trifluoromethyl)-2-cyclobutylbenzo[b]thiophenium bromide, S-(trifluoromethyl)-2-cyclobutylbenzo[b]thiophenium iodide, S-(trifluoromethyl)-2-cyclobutylbenzo[b]thiophenium perchlorate, S-(trifluoromethyl)-2-cyclobutylbenzo[b]thiophenium perbromate, S-(trifluoromethyl)-2-cyclobutylbenzo[b]thiophenium periodate, S-(trifluoromethyl)-2-cyclobutylbenzo[b]thiophenium cyanide, S-(trifluoromethyl)-2-cyclobutylbenzo[b]thiophenium hydrogensulfate, S-(trifluoromethyl)-2-cyclobutylbenzo[b]thiophenium acetate, S-(trifluoromethyl)-2-cyclobutylbenzo[b]thiophenium trifluoroacetate, S-(trifluoromethyl)-2-cyclobutylbenzo[b]thiophenium methanesulfonate, S-(trifluoromethyl)-2-cyclobutylbenzo[b]thiophenium trifluoromethanesulfonate, S-(trifluoromethyl)-2-cyclobutylbenzo[b]thiophenium tetrafluoroborate, S-(trifluoromethyl)-2-n-pentylbenzo[b]thiophenium fluolid, S-(trifluoromethyl)-2-n-pentylbenzo[b]thiophenium chloride, S-(trifluoromethyl)-2-n-pentylbenzo[b]thiophenium bromide, S-(trifluoromethyl)-2-n-pentylbenzo[b]thiophenium iodide, S-(trifluoromethyl)-2-n-pentylbenzo[b]thiophenium perchlorate, S-(trifluoromethyl)-2-n-pentylbenzo[b]thiophenium perbromate, S-(trifluoromethyl)-2-n-pentylbenzo[b]thiophenium periodate, S-(trifluoromethyl)-2-n-pentylbenzo[b]thiophenium cyanide, S-(trifluoromethyl)-2-n-pentylbenzo[b]thiophenium hydrogensulfate, S-(trifluoromethyl)-2-n-pentylbenzo[b]thiophenium acetate, S-(trifluoromethyl)-2-n-pentylbenzo[b]thiophenium trifluoroacetate, S-(trifluoromethyl)-2-n-pentylbenzo[b]thiophenium methanesulfonate, S-(trifluoromethyl)-2-n-pentylbenzo[b]thiophenium trifluoromethanesulfonate, S-(trifluoromethyl)-2-n-pentylbenzo[b]thiophenium tetrafluoroborate, S-(trifluoromethyl)-2-cyclopentylbenzo[b]thiophenium fluolid, S-(trifluoromethyl)-2-cyclopentylbenzo[b]thiophenium chloride, S-(trifluoromethyl)-2-cyclopentylbenzo[b]thiophenium bromide, S-(trifluoromethyl)-2-cyclopentylbenzo[b]thiophenium iodide, S-(trifluoromethyl)-2-cyclopentylbenzo[b]thiophenium perchlorate, S-(trifluoromethyl)-2-cyclopentylbenzo[b]thiophenium perbromate, S-(trifluoromethyl)-2-cyclopentylbenzo[b]thiophenium periodate, S-(trifluoromethyl)-2-cyclopentylbenzo[b]thiophenium cyanide, S-(trifluoromethyl)-2-cyclopentylbenzo[b]thiophenium hydrogensulfate, S-(trifluoromethyl)-2-cyclopentylbenzo[b]thiophenium acetate, S-(trifluoromethyl)-2-cyclopentylbenzo[b]thiophenium trifluoroacetate, S-(trifluoromethyl)-2-cyclopentylbenzo[b]thiophenium methanesulfonate, S-(trifluoromethyl)-2-cyclopentylbenzo[b]thiophenium trifluoromethanesulfonate, S-(trifluoromethyl)-2-cyclopentylbenzo[b]thiophenium tetrafluoroborate, S-(trifluoromethyl)-2-n-hexylbenzo[b]thiophenium fluolid, S-(trifluoromethyl)-2-n-hexylbenzo[b]thiophenium chloride, S-(trifluoromethyl)-2-n-hexylbenzo[b]thiophenium bromide, S-(trifluoromethyl)-2-n-hexylbenzo[b]thiophenium iodide, S-(trifluoromethyl)-2-n-hexylbenzo[b]thiophenium perchlorate, S-(trifluoromethyl)-2-n-hexylbenzo[b]thiophenium perbromate, S-(trifluoromethyl)-2-n-hexylbenzo[b]thiophenium periodate, S-(trifluoromethyl)-2-n-hexylbenzo[b]thiophenium cyanide, S-(trifluoromethyl)-2-n-hexylbenzo[b]thiophenium hydrogensulfate, S-(trifluoromethyl)-2-n-hexylbenzo[b]thiophenium acetate, S-(trifluoromethyl)-2-n-hexylbenzo[b]thiophenium trifluoroacetate, S-(trifluoromethyl)-2-n-hexylbenzo[b]thiophenium methanesulfonate, S-(trifluoromethyl)-2-n-hexylbenzo[b]thiophenium trifluoromethanesulfonate, S-(trifluoromethyl)-2-n-hexylbenzo[b]thiophenium tetrafluoroborate, S-(trifluoromethyl)-2-cyclohexylbenzo[b]thiophenium fluolid, S-(trifluoromethyl)-2-cyclohexylbenzo[b]thiophenium chloride, S-(trifluoromethyl)-2-cyclohexylbenzo[b]thiophenium bromide, S-(trifluoromethyl)-2-cyclohexylbenzo[b]thiophenium iodide, S-(trifluoromethyl)-2-cyclohexylbenzo[b]thiophenium perchlorate, S-(trifluoromethyl)-2-cyclohexylbenzo[b]thiophenium perbromate, S-(trifluoromethyl)-2-cyclohexylbenzo[b]thiophenium periodate, S-(trifluoromethyl)-2-cyclohexylbenzo[b]thiophenium cyanide, S-(trifluoromethyl)-2-cyclohexylbenzo[b]thiophenium hydrogensulfate, S-(trifluoromethyl)-2-cyclohexylbenzo[b]thiophenium acetate, S-(trifluoromethyl)-2-cyclohexylbenzo[b]thiophenium trifluoroacetate, S-(trifluoromethyl)-2-cyclohexylbenzo[b]thiophenium methanesulfonate, S-(trifluoromethyl)-2-cyclohexylbenzo[b]thiophenium trifluoromethanesulfonate, S-(trifluoromethyl)-2-cyclohexylbenzo[b]thiophenium tetrafluoroborate, S-(trifluoromethyl)-2-n-heptylbenzo[b]thiophenium fluolid, S-(trifluoromethyl)-2-n-heptylbenzo[b]thiophenium chloride, S-(trifluoromethyl)-2-n-heptylbenzo[b]thiophenium bromide, S-(trifluoromethyl)-2-n-heptylbenzo[b]thiophenium iodide, S-(trifluoromethyl)-2-n-heptylbenzo[b]thiophenium perchlorate, S-(trifluoromethyl)-2-n-heptylbenzo[b]thiophenium perbromate, S-(trifluoromethyl)-2-n-heptylbenzo[b]thiophenium periodate, S-(trifluoromethyl)-2-n-heptylbenzo[b]thiophenium cyanide, S-(trifluoromethyl)-2-n-heptylbenzo[b]thiophenium hydrogensulfate, S-(trifluoromethyl)-2-n-heptylbenzo[b]thiophenium acetate, S-(trifluoromethyl)-2-n-heptylbenzo[b]thiophenium trifluoroacetate, S-(trifluoromethyl)-2-n-heptylbenzo[b]thiophenium methanesulfonate, S-(trifluoromethyl)-2-n-heptylbenzo[b]thiophenium trifluoromethanesulfonate, S-(trifluoromethyl)-2-n-heptylbenzo[b]thiophenium tetrafluoroborate, S-(trifluoromethyl)-2-cycloheptylbenzo[b]thiophenium fluolid, S-(trifluoromethyl)-2-cycloheptylbenzo[b]thiophenium chloride, S-(trifluoromethyl)-2-cycloheptylbenzo[b]thiophenium bromide, S-(trifluoromethyl)-2-cycloheptylbenzo[b]thiophenium iodide, S-(trifluoromethyl)-2-cycloheptylbenzo[b]thiopheniumperbromate, S-(trifluoromethyl)-2-cycloheptylbenzo[b]thiophenium periodate, S-(trifluoromethyl)-2-cycloheptylbenzo[b]thiophenium cyanide, S-(trifluoromethyl)-2-cycloheptylbenzo[b]thiophenium hydrogensulfate, S-(trifluoromethyl)-2-cycloheptylbenzo[b]thiophenium acetate, S-(trifluoromethyl)-2-cycloheptylbenzo[b]thiophenium trifluoroacetate, S-(trifluoromethyl)-2-cycloheptylbenzo[b]thiophenium methanesulfonate, S-(trifluoromethyl)-2-cycloheptylbenzo[b]thiophenium trifluoromethanesulfonate, S-(trifluoromethyl)-2-cycloheptylbenzo[b]thiophenium tetrafluoroborate, S-(trifluoromethyl)-2-cycloheptylbenzo[b]thiophenium fluolid, S-(trifluoromethyl)-2-cycloheptylbenzo[b]thiophenium chloride, S-(trifluoromethyl)-2-cycloheptylbenzo[b]thiophenium bromide, S-(trifluoromethyl)-2-cycloheptylbenzo[b]thiophenium iodide, S-(trifluoromethyl)-2-cycloheptylbenzo[b]thiophenium perchlorate, S-(trifluoromethyl)-2-cycloheptylbenzo[b]thiophenium perbromate, S-(trifluoromethyl)-2-cycloheptylbenzo[b]

thiophenium periodate, S-(trifluoromethyl)-2-cycloheptylbenzo[b]thiophenium cyanide, S-(trifluoromethyl)-2-cycloheptylbenzo[b]thiophenium hydrogensulfate, S-(trifluoromethyl)-2-cycloheptylbenzo[b]thiophenium acetate, S-(trifluoromethyl)-2-cycloheptylbenzo[b]thiophenium trifluoroacetate, S-(trifluoromethyl)-2-cycloheptylbenzo[b]thiophenium methanesulfonate, S-(trifluoromethyl)-2-cycloheptylbenzo[b]thiophenium trifluoromethanesulfonate, S-(trifluoromethyl)-2-cycloheptylbenzo[b]thiophenium tetrafluoroborate, S-(trifluoromethyl)-2-methyl-4-methylbenzo[b]thiophenium chloride, S-(trifluoromethyl)-2-methyl-4-methylbenzo[b]thiophenium bromide, S-(trifluoromethyl)-2-methyl-4-methylbenzo[b]thiophenium trifluoromethanesulfonate, S-(trifluoromethyl)-2-methyl-4-methylbenzo[b]thiophenium tetrafluoroborate, S-(trifluoromethyl)-2-ethyl-4-methylbenzo[b]thiophenium chloride, S-(trifluoromethyl)-2-ethyl-4-methyl[b]thiophenium bromide, S-(trifluoromethyl)-2-ethyl-4-methylbenzo[b]thiophenium trifluoromethanesulfonate, S-(trifluoromethyl)-2-ethyl-4-methylbenzo[b]thiophenium tetrafluoroborate, S-(trifluoromethyl)-2-n-propyl-4-methylbenzo[b]thiophenium chloride, S-(trifluoromethyl)-2-n-propyl-4-methylbenzo[b]thiophenium bromide, S-(trifluoromethyl)-2-n-propyl-4-methylbenzo[b]thiophenium trifluoromethanesulfonate, S-(trifluoromethyl)-2-n-propyl-4-methylbenzo[b]thiophenium tetrafluoroborate, S-(trifluoromethyl)-2-iso-propyl-4-methylbenzo[b]thiophenium chloride, S-(trifluoromethyl)-2-iso-propyl-4-methylbenzo[b]thiophenium bromide, S-(trifluoromethyl)-2-iso-propyl-4-methylbenzo[b]thiophenium trifluoromethanesulfonate, S-(trifluoromethyl)-2-iso-propyl-4-methylbenzo[b]thiophenium tetrafluoroborate, S-(trifluoromethyl)-2-n-butyl-4-methylbenzo[b]thiophenium chloride, S-(trifluoromethyl)-2-n-butyl-4-methylbenzo[b]thiophenium bromide, S-(trifluoromethyl)-2-n-butyl-4-methylbenzo[b]thiophenium trifluoromethanesulfonate, S-(trifluoromethyl)-2-n-butyl-4-methylbenzo[b]thiophenium tetrafluoroborate, S-(trifluoromethyl)-2-tert-butyl-4-methylbenzo[b]thiophenium chloride, S-(trifluoromethyl)-2-tert-butyl-4-methylbenzo[b]thiophenium bromide, S-(trifluoromethyl)-2-tert-butyl-4-methylbenzo[b]thiophenium trifluoromethanesulfonate, S-(trifluoromethyl)-2-tert-butyl-4-methylbenzo[b]thiophenium tetrafluoroborate, S-(trifluoromethyl)-2-cyclopropyl-4-methylbenzo[b]thiophenium chloride, S-(trifluoromethyl)-2-cyclopropyl-4-methylbenzo[b]thiophenium bromide, S-(trifluoromethyl)-2-cyclopropyl-4-methylbenzo[b]thiophenium trifluoromethanesulfonate, S-(trifluoromethyl)-2-cyclopropyl-4-Methylbenzo[b]thiophenium tetrafluoroborate, S-(trifluoromethyl)-2-cyclobutyl-4-methylbenzo[b]thiophenium chloride, S-(trifluoromethyl)-2-cyclobutyl-4-methylbenzo[b]thiophenium bromide, S-(trifluoromethyl)-2-cyclobutyl-4-methylbenzo[b]thiophenium trifluoromethanesulfonate, S-(trifluoromethyl)-2-cyclobutyl-4-methylbenzo[b]thiophenium tetrafluoroborate, S-(trifluoromethyl)-2-cyclopentyl-4-methylbenzo[b]thiophenium chloride, S-(trifluoromethyl)-2-cyclopentyl-4-methylbenzo[b]thiophenium bromide, S-(trifluoromethyl)-2-cyclopentyl-4-methylbenzo[b]thiophenium trifluoromethanesulfonate, S-(trifluoromethyl)-2-cyclopentyl-4-methylbenzo[b]thiophenium tetrafluoroborate, S-(trifluoromethyl)-2-cyclohexyl-4-methylbenzo[b]thiophenium chloride, S-(trifluoromethyl)-2-cyclohexyl-4-methylbenzo[b]thiophenium bromide, S-(trifluoromethyl)-2-cyclohexyl-4-methylbenzo[b]thiophenium trifluoromethanesulfonate, S-(trifluoromethyl)-2-cyclohexyl-4-methylbenzo[b]thiophenium tetrafluoroborate, S-(trifluoromethyl)-2-cycloheptyl-4-methylbenzo[b]thiophenium chloride, S-(trifluoromethyl)-2-cycloheptyl-4-methylbenzo[b]thiophenium bromide, S-(trifluoromethyl)-2-cycloheptyl-4-methylbenzo[b]thiophenium trifluoromethanesulfonate, S-(trifluoromethyl)-2-cycloheptyl-4-methylbenzo[b]thiophenium tetrafluoroborate, S-(trifluoromethyl)-2-methyl-5-methylbenzo[b]thiophenium chloride, S-(trifluoromethyl)-2-methyl-5-methylbenzo[b]thiophenium bromide, S-(trifluoromethyl)-2-methyl-5-methylbenzo[b]thiophenium trifluoromethanesulfonate, S-(trifluoromethyl)-2-methyl-5-methylbenzo[b]thiophenium tetrafluoroborate, S-(trifluoromethyl)-2-ethyl-5-methylbenzo[b]thiophenium chloride, S-(trifluoromethyl)-2-ethyl-5-methyl[b]thiophenium bromide, S-(trifluoromethyl)-2-ethyl-5-methylbenzo[b]thiophenium trifluoromethanesulfonate, S-(trifluoromethyl)-2-ethyl-5-methylbenzo[b]thiophenium tetrafluoroborate, S-(trifluoromethyl)-2-n-propyl-5-methylbenzo[b]thiophenium chloride, S-(trifluoromethyl)-2-n-propyl-5-methylbenzo[b]thiophenium bromide, S-(trifluoromethyl)-2-n-propyl-5-methylbenzo[b]thiophenium trifluoromethanesulfonate, S-(trifluoromethyl)-2-n-propyl-5-methylbenzo[b]thiophenium tetrafluoroborate, S-(trifluoromethyl)-2-iso-propyl-5-methylbenzo[b]thiophenium chloride, S-(trifluoromethyl)-2-iso-propyl-5-methylbenzo[b]thiophenium bromide, S-(trifluoromethyl)-2-iso-propyl-5-methylbenzo[b]thiophenium trifluoromethanesulfonate, S-(trifluoromethyl)-2-iso-propyl-5-methylbenzo[b]thiophenium tetrafluoroborate, S-(trifluoromethyl)-2-n-butyl-5-methylbenzo[b]thiophenium chloride, S-(trifluoromethyl)-2-n-butyl-5-methylbenzo[b]thiophenium bromide, S-(trifluoromethyl)-2-n-butyl-5-methylbenzo[b]thiophenium trifluoromethanesulfonate, S-(trifluoromethyl)-2-n-butyl-5-methylbenzo[b]thiophenium tetrafluoroborate, S-(trifluoromethyl)-2-tert-butyl-5-methylbenzo[b]thiophenium chloride, S-(trifluoromethyl)-2-tert-butyl-5-methylbenzo[b]thiophenium bromide, S-(trifluoromethyl)-2-tert-butyl-5-methylbenzo[b]thiophenium trifluoromethanesulfonate, S-(trifluoromethyl)-2-tert-butyl-5-methylbenzo[b]thiophenium tetrafluoroborate, S-(trifluoromethyl)-2-cyclopropyl-5-methylbenzo[b]thiophenium chloride, S-(trifluoromethyl)-2-cyclopropyl-5-methylbenzo[b]thiophenium bromide, S-(trifluoromethyl)-2-cyclopropyl-5-methylbenzo[b]thiophenium trifluoromethanesulfonate, S-(trifluoromethyl)-2-cyclopropyl-5-methylbenzo[b]thiophenium tetrafluoroborate, S-(trifluoromethyl)-2-cyclobutyl-5-methylbenzo[b]thiophenium chloride, S-(trifluoromethyl)-2-cyclobutyl-5-methylbenzo[b]thiophenium bromide, S-(trifluoromethyl)-2-cyclobutyl-5-methylbenzo[b]thiophenium trifluoromethanesulfonate, S-(trifluoromethyl)-2-cyclobutyl-5-methylbenzo[b]thiophenium tetrafluoroborate, S-(trifluoromethyl)-2-cyclopentyl-5-methylbenzo[b]thiophenium chloride, S-(trifluoromethyl)-2-cyclopentyl-5-methylbenzo[b]thiophenium bromide, S-(trifluoromethyl)-2-cyclopentyl-5-methylbenzo[b]thiophenium trifluoromethanesulfonate, S-(trifluoromethyl)-2-cyclopentyl-5-methylbenzo[b]thiophenium tetrafluoroborate, S-(trifluoromethyl)-2-cyclohexyl-5-methylbenzo[b]thiophenium chloride, S-(trifluoromethyl)-2-cyclohexyl-5-methylbenzo[b]thiophenium bromide, S-(trifluoromethyl)-2-cyclohexyl-5-methylbenzo[b]thiophenium trifluoromethanesulfonate, S-(trifluoromethyl)-2-cyclohexyl-5-methylbenzo[b]thiophenium tetrafluoroborate, S-(trifluoromethyl)-2-cycloheptyl-5-methylbenzo[b]thiophenium chloride, S-(trifluoromethyl)-2-cycloheptyl-5-methylbenzo[b]thiophenium bromide, S-(trifluoromethyl)-2-cycloheptyl-5-methylbenzo[b]thiophenium trifluoromethanesulfonate, S-(trifluoromethyl)-2-cycloheptyl-5-methylbenzo[b]thiophenium tetrafluoroborate, S-(trifluoromethyl)-2-methyl-6-methylbenzo[b]thiophenium chloride, S-(trifluoromethyl)-2-methyl-6-methylbenzo[b]thiophenium bromide, S-(trifluoromethyl)-2-methyl-6-methylbenzo[b]thiophenium trifluoromethanesulfonate, S-(trifluoromethyl)-2-methyl-6-methylbenzo[b]thiophenium tetrafluoroborate, S-(trifluoromethyl)-2-ethyl-6-methylbenzo[b]thiophenium chloride, S-(trifluoromethyl)-2-ethyl-6-methyl[b]thiophenium bromide, S-(trifluoromethyl)-2-ethyl-6-methylbenzo[b]thiophenium trifluoromethanesulfonate, S-(trifluoromethyl)-2-ethyl-6-methylbenzo[b]thiophenium tetrafluoroborate, S-(trifluoromethyl)-2-n-propyl-6-methylbenzo[b]thiophenium chloride, S-(trifluoromethyl)-2-n-propyl-6-methylbenzo[b]thiophenium bromide, S-(trifluoromethyl)-2-n-propyl-6-methylbenzo[b]thiophenium trifluoromethanesulfonate, S-(trifluoromethyl)-2-n-propyl-6-methylbenzo[b]thiophenium tetrafluoroborate, S-(trifluoromethyl)-2-iso-propyl-6-methylbenzo[b]thiophenium chloride, S-(trifluoromethyl)-2-iso-propyl-6-methylbenzo[b]thiophenium bromide, S-(trifluoromethyl)-2-iso-propyl-6-methylbenzo[b]thiophenium trifluoromethanesulfonate, S-(trifluoromethyl)-2-iso-propyl-6-methylbenzo[b]thiophenium tetrafluoroborate, S-(trifluoromethyl)-2-n-butyl-6-methylbenzo[b]thiophenium chloride, S-(trifluoromethyl)-2-n-butyl-6-methylbenzo[b]thiophenium bromide, S-(trifluoromethyl)-2-n-butyl-6-methylbenzo[b]thiophenium trifluoromethanesulfonate, S-(trifluoromethyl)-2-n-butyl-6-methylbenzo[b]thiophenium tetrafluoroborate, S-(trifluoromethyl)-2-tert-butyl-6-methylbenzo[b]thiophenium chloride, S-(trifluoromethyl)-2-tert-butyl-6-methylbenzo[b]thiophenium bromide, S-(trifluoromethyl)-2-tert-butyl-6-methylbenzo[b]thiophenium trifluoromethanesulfonate, S-(trifluoromethyl)-2-tert-butyl-6-methylbenzo[b]thiophenium tetrafluoroborate, S-(trifluoromethyl)-2-cyclopropyl-6-methylbenzo[b]thiophenium chloride, S-(trifluoromethyl)-2-cyclopropyl-6-methylbenzo[b]thiophenium bromide, S-(trifluoromethyl)-2-cyclopropyl-6-methylbenzo[b]thiophenium trifluoromethanesulfonate, S-(trifluoromethyl)-2-cyclopropyl-6-methylbenzo[b]thiophenium tetrafluoroborate, S-(trifluoromethyl)-2-cyclobutyl-6-methylbenzo[b]thiophenium chloride, S-(trifluoromethyl)-2-cyclobutyl-6-methylbenzo[b]thiophenium bromide, S-(trifluoromethyl)-2-cyclobutyl-6-methylbenzo[b]thiophenium trifluoromethanesulfonate, S-(trifluoromethyl)-2-cyclobutyl-6-methylbenzo[b]thiophenium tetrafluoroborate, S-(trifluoromethyl)-2-cyclopentyl-6-methylbenzo[b]thiophenium chloride, S-(trifluoromethyl)-2-cyclopentyl-6-methylbenzo[b]thiophenium bromide, S-(trifluoromethyl)-2-cyclopentyl-6-methylbenzo[b]thiophenium trifluoromethanesulfonate, S-(trifluoromethyl)-2-cyclopentyl-6-methylbenzo[b]thiophenium tetrafluoroborate, S-(trifluoromethyl)-2-cyclohexyl-6-methylbenzo[b]thiophenium chloride, S-(trifluoromethyl)-2-cyclohexyl-6-methylbenzo[b]thiophenium bromide, S-(trifluoromethyl)-2-cyclohexyl-6-methylbenzo[b]thiophenium trifluoromethanesulfonate, S-(trifluoromethyl)-2-cyclohexyl-6-methylbenzo[b]thiophenium tetrafluoroborate, S-(trifluoromethyl)-2-cycloheptyl-6-methylbenzo[b]thiophenium chloride, S-(trifluoromethyl)-2-cycloheptyl-6-methylbenzo[b]thiophenium bromide, S-(trifluoromethyl)-2-cycloheptyl-6-methylbenzo[b]thiophenium trifluoromethanesulfonate, S-(trifluoromethyl)-2-cycloheptyl-6-methylbenzo[b]thiophenium tetrafluoroborate, S-(trifluoromethyl)-2-methyl-4-ethylbenzo[b]thiophenium chloride, S-(trifluoromethyl)-2-methyl-4-ethylbenzo[b]thiophenium bromide, S-(trifluoromethyl)-2-methyl-4-ethylbenzo[b]thiophenium trifluoromethanesulfonate, S-(trifluoromethyl)-2-methyl-4-ethylbenzo[b]thiophenium tetrafluoroborate, S-(trifluoromethyl)-2-ethyl-4-ethylbenzo[b]thiophenium chloride, S-(trifluoromethyl)-2-ethyl-4-ethylbenzo[b]thiophenium bromide, S-(trifluoromethyl)-2-ethyl-4-ethylbenzo[b]thiophenium trifluoromethanesulfonate, S-(trifluoromethyl)-2-ethyl-4-ethylbenzo[b]thiophenium tetrafluoroborate, S-(trifluoromethyl)-2-n-propyl-4-ethylbenzo[b]thiophenium chloride, S-(trifluoromethyl)-2-n-propyl-4-ethylbenzo[b]thiophenium bromide, S-(trifluoromethyl)-2-n-propyl-4-ethylbenzo[b]thiophenium trifluoromethanesulfonate, S-(trifluoromethyl)-2-n-propyl-4-ethylbenzo[b]thiophenium tetrafluoroborate, S-(trifluoromethyl)-2-iso-propyl-4-ethylbenzo[b]thiophenium chloride, S-(trifluoromethyl)-2-iso-propyl-4-ethylbenzo[b]thiophenium bromide, S-(trifluoromethyl)-2-iso-propyl-4-ethylbenzo[b]thiophenium trifluoromethanesulfonate, S-(trifluoromethyl)-2-iso-propyl-4-ethylbenzo[b]thiophenium tetrafluoroborate, S-(trifluoromethyl)-2-n-butyl-4-ethylbenzo[b]thiophenium chloride, S-(trifluoromethyl)-2-n-butyl-4-ethylbenzo[b]thiophenium bromide, S-(trifluoromethyl)-2-n-butyl-4-ethylbenzo[b]thiophenium trifluoromethanesulfonate, S-(trifluoromethyl)-2-n-butyl-4-ethylbenzo[b]thiophenium tetrafluoroborate, S-(trifluoromethyl)-2-tert-butyl-4-ethylbenzo[b]thiophenium chloride, S-(trifluoromethyl)-2-tert-butyl-4-ethylbenzo[b]thiophenium bromide, S-(trifluoromethyl)-2-tert-butyl-4-ethylbenzo[b]thiophenium trifluoromethanesulfonate, S-(trifluoromethyl)-2-tert-butyl-4-ethylbenzo[b]thiophenium tetrafluoroborate, S-(trifluoromethyl)-2-cyclopropyl-4-ethylbenzo[b]thiophenium chloride, S-(trifluoromethyl)-2-cyclopropyl-4-ethylbenzo[b]thiophenium bromide, S-(trifluoromethyl)-2-cyclopropyl-4-ethylbenzo[b]thiophenium trifluoromethanesulfonate, S-(trifluoromethyl)-2-cyclopropyl-4-ethylbenzo[b]thiophenium tetrafluoroborate, S-(trifluoromethyl)-2-cyclobutyl-4-ethylbenzo[b]thiophenium chloride, S-(trifluoromethyl)-2-cyclobutyl-4-ethylbenzo[b]thiophenium bromide, S-(trifluoromethyl)-2-cyclobutyl-4-ethylbenzo[b]thiophenium trifluoromethanesulfonate, S-(trifluoromethyl)-2-cyclobutyl-4-ethylbenzo[b]thiophenium tetrafluoroborate, S-(trifluoromethyl)-2-cyclopentyl-4-ethylbenzo[b]thiophenium chloride, S-(trifluoromethyl)-2-cyclopentyl-4-ethylbenzo[b]thiophenium bromide, S-(trifluoromethyl)-2-cyclopentyl-4-ethylbenzo[b]thiophenium trifluoromethanesulfonate, S-(trifluoromethyl)-2-cyclopentyl-4-ethylbenzo[b]thiophenium tetrafluoroborate, S-(trifluoromethyl)-2-cyclohexyl-4-ethylbenzo[b]thiophenium chloride, S-(trifluoromethyl)-2-cyclohexyl-4-ethylbenzo[b]thiophenium bromide, S-(trifluoromethyl)-2-cyclohexyl-4-ethylbenzo[b]thiophenium trifluoromethanesulfonate, S-(trifluoromethyl)-2-cyclohexyl-4-ethylbenzo[b]thiophenium tetrafluoroborate, S-(trifluoromethyl)-2-cycloheptyl-4-ethylbenzo[b]thiophenium chloride, S-(trifluoromethyl)-2-cycloheptyl-4-ethylbenzo[b]thiophenium bromide, S-(trifluoromethyl)-2-cycloheptyl-4-ethylbenzo[b]thiophenium trifluoromethanesulfonate, S-(trifluoromethyl)-2-cycloheptyl-4-ethylbenzo[b]thiophenium tetrafluoroborate, S-(trifluoromethyl)-2-methyl-5-ethylbenzo[b]thiophenium chloride, S-(trifluoromethyl)-2-methyl-5-ethylbenzo[b]thiophenium bromide, S-(trifluoromethyl)-2-methyl-5-ethylbenzo[b]thiophenium trifluoromethanesulfonate, S-(trifluoromethyl)-2-methyl-5-ethylbenzo[b]thiophenium tetrafluoroborate, S-(trifluoromethyl)-2-ethyl-5-ethylbenzo[b]thiophenium chloride, S-(trifluoromethyl)-2-ethyl-5-ethylbenzo[b]thiophenium bromide, S-(trifluoromethyl)-2-ethyl-5-ethylbenzo[b]thiophenium trifluoromethanesulfonate, S-(trifluoromethyl)-2-ethyl-5-ethylbenzo[b]thiophenium tetrafluoroborate, S-(trifluoromethyl)-2-n-propyl-5-ethylbenzo[b]thiophenium chloride, S-(trifluoromethyl)-2-n-propyl-5-ethylbenzo[b]thiophenium bromide, S-(trifluoromethyl)-2-n-propyl-5-ethylbenzo[b]thiophenium trifluoromethanesulfonate, S-(trifluoromethyl)-2-n-propyl-5-ethylbenzo[b]thiophenium tetrafluoroborate, S-(trifluoromethyl)-2-iso-propyl-5-ethylbenzo[b]thiophenium chloride, S-(trifluoromethyl)-2-iso-propyl-5-ethylbenzo[b]thiophenium bromide, S-(trifluoromethyl)-2-iso-propyl-5-ethylbenzo[b]thiophenium trifluoromethanesulfonate, S-(trifluoromethyl)-2-iso-propyl-5-ethylbenzo[b]thiophenium tetrafluoroborate, S-(trifluoromethyl)-2-n-butyl-5-ethylbenzo[b]thiophenium chloride, S-(trifluoromethyl)-2-n-butyl-5-ethylbenzo[b]thiophenium bromide, S-(trifluoromethyl)-2-n-butyl-5-ethylbenzo[b]thiophenium trifluoromethanesulfonate, S-(trifluoromethyl)-2-n-butyl-5-ethylbenzo[b]thiophenium tetrafluoroborate, S-(trifluoromethyl)-2-tert-butyl-5-ethylbenzo[b]thiophenium chloride, S-(trifluoromethyl)-2-tert-butyl-5-ethylbenzo[b]thiophenium bromide, S-(trifluoromethyl)-2-tert-butyl-5-ethylbenzo[b]thiophenium trifluoromethanesulfonate, S-(trifluoromethyl)-2-tert-butyl-5-ethylbenzo[b]thiophenium tetrafluoroborate, S-(trifluoromethyl)-2-cyclopropyl-5-ethylbenzo[b]thiophenium chloride, S-(trifluoromethyl)-2-cyclopropyl-5-ethylbenzo[b]thiophenium bromide, S-(trifluoromethyl)-2-cyclopropyl-5-ethylbenzo[b]thiophenium trifluoromethanesulfonate, S-(trifluoromethyl)-2-cyclopropyl-5-ethylbenzo[b]thiophenium tetrafluoroborate, S-(trifluoromethyl)-2-cyclobutyl-5-ethylbenzo[b]thiophenium chloride, S-(trifluoromethyl)-2-cyclobutyl-5-ethylbenzo[b]thiophenium bromide, S-(trifluoromethyl)-2-cyclobutyl-5-ethylbenzo[b]thiophenium trifluoromethanesulfonate, S-(trifluoromethyl)-2-cyclobutyl-5-ethylbenzo[b]thiophenium tetrafluoroborate, S-(trifluoromethyl)-2-cyclopentyl-5-ethylbenzo[b]thiophenium chloride, S-(trifluoromethyl)-2-cyclopentyl-5-ethylbenzo[b]thiophenium bromide, S-(trifluoromethyl)-2-cyclopentyl-5-ethylbenzo[b]thiophenium trifluoromethanesulfonate, S-(trifluoromethyl)-2-cyclopentyl-5-ethylbenzo[b]thiophenium tetrafluoroborate, S-(trifluoromethyl)-2-cyclohexyl-5-ethylbenzo[b]thiophenium chloride, S-(trifluoromethyl)-2-cyclohexyl-5-ethylbenzo[b]thiophenium bromide, S-(trifluoromethyl)-2-cyclohexyl-5-ethylbenzo[b]thiophenium trifluoromethanesulfonate, S-(trifluoromethyl)-2-cyclohexyl-5-ethylbenzo[b]thiophenium tetrafluoroborate, S-(trifluoromethyl)-2-cycloheptyl-5-ethylbenzo[b]thiophenium chloride, S-(trifluoromethyl)-2-cycloheptyl-5-ethylbenzo[b]thiophenium bromide, S-(trifluoromethyl)-2-cycloheptyl-5-ethylbenzo[b]thiophenium trifluoromethanesulfonate, S-(trifluoromethyl)-2-cycloheptyl-5-ethylbenzo[b]thiophenium tetrafluoroborate, S-(trifluoromethyl)-2-methyl-6-ethylbenzo[b]thiophenium chloride, S-(trifluoromethyl)-2-methyl-6-ethylbenzo[b]thiophenium bromide, S-(trifluoromethyl)-2-methyl-6-ethylbenzo[b]thiophenium trifluoromethanesulfonate, S-(trifluoromethyl)-2-methyl-6-ethylbenzo[b]thiophenium tetrafluoroborate, S-(trifluoromethyl)-2-ethyl-6-ethylbenzo[b]thiophenium chloride, S-(trifluoromethyl)-2-ethyl-6-ethylbenzo[b]thiophenium bromide, S-(trifluoromethyl)-2-ethyl-6-ethylbenzo[b]thiophenium trifluoromethanesulfonate, S-(trifluoromethyl)-2-ethyl-6-ethylbenzo[b]thiophenium tetrafluoroborate, S-(trifluoromethyl)-2-n-propyl-6-ethylbenzo[b]thiophenium chloride, S-(trifluoromethyl)-2-n-propyl-6-ethylbenzo[b]thiophenium bromide, S-(trifluoromethyl)-2-n-propyl-6-ethylbenzo[b]thiophenium trifluoromethanesulfonate, S-(trifluoromethyl)-2-n-propyl-6-ethylbenzo[b]thiophenium tetrafluoroborate, S-(trifluoromethyl)-2-iso-propyl-6-ethylbenzo[b]thiophenium chloride, S-(trifluoromethyl)-2-iso-propyl-6-ethylbenzo[b]thiophenium bromide, S-(trifluoromethyl)-2-iso-propyl-6-ethylbenzo[b]thiophenium trifluoromethanesulfonate, S-(trifluoromethyl)-2-iso-propyl-6-ethylbenzo[b]thiophenium tetrafluoroborate, S-(trifluoromethyl)-2-n-butyl-6-ethylbenzo[b]thiophenium chloride, S-(trifluoromethyl)-2-n-butyl-6-ethylbenzo[b]thiophenium bromide, S-(trifluoromethyl)-2-n-butyl-6-ethylbenzo[b]thiophenium trifluoromethanesulfonate, S-(trifluoromethyl)-2-n-butyl-6-ethylbenzo[b]thiophenium tetrafluoroborate, S-(trifluoromethyl)-2-tert-butyl-6-ethylbenzo[b]thiophenium chloride, S-(trifluoromethyl)-2-tert-butyl-6-ethylbenzo[b]thiophenium bromide, S-(trifluoromethyl)-2-tert-butyl-6-ethylbenzo[b]thiophenium trifluoromethanesulfonate, S-(trifluoromethyl)-2-tert-butyl-6-ethylbenzo[b]thiophenium tetrafluoroborate, S-(trifluoromethyl)-2-cyclopropyl-6-ethylbenzo[b]thiophenium chloride, S-(trifluoromethyl)-2-cyclopropyl-6-ethylbenzo[b]thiophenium bromide, S-(trifluoromethyl)-2-cyclopropyl-6-ethylbenzo[b]thiophenium trifluoromethanesulfonate, S-(trifluoromethyl)-2-cyclopropyl-6-ethylbenzo[b]thiophenium tetrafluoroborate, S-(trifluoromethyl)-2-cyclobutyl-6-ethylbenzo[b]thiophenium chloride, S-(trifluoromethyl)-2-cyclobutyl-6-ethylbenzo[b]thiophenium bromide, S-(trifluoromethyl)-2-cyclobutyl-6-ethylbenzo[b]thiophenium trifluoromethanesulfonate, S-(trifluoromethyl)-2-cyclobutyl-6-ethylbenzo[b]thiophenium tetrafluoroborate, S-(trifluoromethyl)-2-cyclopentyl-6-ethylbenzo[b]thiophenium chloride, S-(trifluoromethyl)-2-cyclopentyl-6-ethylbenzo[b]thiophenium bromide, S-(trifluoromethyl)-2-cyclopentyl-6-ethylbenzo[b]thiophenium trifluoromethanesulfonate, S-(trifluoromethyl)-2-cyclopentyl-6-ethylbenzo[b]thiophenium tetrafluoroborate, S-(trifluoromethyl)-2-cyclohexyl-6-ethylbenzo[b]thiophenium chloride, S-(trifluoromethyl)-2-cyclohexyl-6-ethylbenzo[b]thiophenium bromide, S-(trifluoromethyl)-2-cyclohexyl-6-ethylbenzo[b]thiophenium trifluoromethanesulfonate, S-(trifluoromethyl)-2-cyclohexyl-6-ethylbenzo[b]thiophenium tetrafluoroborate, S-(trifluoromethyl)-2-cycloheptyl-6-ethylbenzo[b]thiophenium chloride, S-(trifluoromethyl)-2-cycloheptyl-6-ethylbenzo[b]thiophenium bromide, S-(trifluoromethyl)-2-cycloheptyl-6-ethylbenzo[b]thiophenium trifluoromethanesulfonate, S-(trifluoromethyl)-2-cycloheptyl-6-ethylbenzo[b]thiophenium tetrafluoroborate, S-(trifluoromethyl)-2-methyl-6-n-propylbenzo[b]thiophenium chloride, S-(trifluoromethyl)-2-methyl-6-n-propylbenzo[b]thiophenium bromide, S-(trifluoromethyl)-2-methyl-6-n-propylbenzo[b]thiophenium trifluoromethanesulfonate, S-(trifluoromethyl)-2-methyl-6-n-propylbenzo[b]thiophenium tetrafluoroborate, S-(trifluoromethyl)-2-ethyl-6-n-propylbenzo[b]thiophenium chloride, S-(trifluoromethyl)-2-ethyl-6-n-propylbenzo[b]thiophenium bromide, S-(trifluoromethyl)-2-ethyl-6-n-propylbenzo[b]thiophenium trifluoromethanesulfonate, S-(trifluoromethyl)-2-ethyl-6-n-propylbenzo[b]thiophenium tetrafluoroborate, S-(trifluoromethyl)-2-n-propyl-6-n-propylbenzo[b]thiophenium chloride, S-(trifluoromethyl)-2-n-propyl-6-n-propylbenzo[b]thiophenium bromide, S-(trifluoromethyl)-2-n-propyl-6-n-propylbenzo[b]thiophenium trifluoromethanesulfonate, S-(trifluoromethyl)-2-n-propyl-6-n-propylbenzo[b]thiophenium tetrafluoroborate, S-(trifluoromethyl)-2-iso-propyl-6-n-propylbenzo[b]thiophenium chloride, S-(trifluoromethyl)-2-iso-propyl-6-n-propylbenzo[b]thiophenium bromide, S-(trifluoromethyl)-2-iso-propyl-6-n-propylbenzo[b]thiophenium trifluoromethanesulfonate, S-(trifluoromethyl)-2-iso-propyl-6-n-propylbenzo[b]thiophenium tetrafluoroborate, S-(trifluoromethyl)-2-n-butyl-6-n-propylbenzo[b]thiophenium chloride, S-(trifluoromethyl)-2-n-butyl-6-n-propylbenzo[b]thiophenium bromide, S-(trifluoromethyl)-2-n-butyl-6-n-propylbenzo[b]thiophenium trifluoromethanesulfonate, S-(trifluoromethyl)-2-n-butyl-6-n-propylbenzo[b]thiophenium tetrafluoroborate, S-(trifluoromethyl)-2-tert-butyl-6-n-propylbenzo[b]thiophenium chloride, S-(trifluoromethyl)-2-tert-butyl-6-n-propylbenzo[b]thiophenium bromide, S-(trifluoromethyl)-2-tert-butyl-6-n-propylbenzo[b]thiophenium trifluoromethanesulfonate, S-(trifluoromethyl)-2-tert-butyl-6-n-propylbenzo[b]thiophenium tetrafluoroborate, S-(trifluoromethyl)-2-cyclopropyl-6-n-propylbenzo[b]thiophenium chloride, S-(trifluoromethyl)-2-cyclopropyl-6-n-propylbenzo[b]thiophenium bromide, S-(trifluoromethyl)-2-cyclopropyl-6-n-propylbenzo[b]thiophenium trifluoromethanesulfonate, S-(trifluoromethyl)-2-cyclopropyl-6-n-propylbenzo[b]thiophenium tetrafluoroborate, S-(trifluoromethyl)-2-cyclobutyl-6-n-propylbenzo[b]thiophenium chloride, S-(trifluoromethyl)-2-cyclobutyl-6-n-propylbenzo[b]thiophenium bromide, S-(trifluoromethyl)-2-cyclobutyl-6-n-propylbenzo[b]thiophenium trifluoromethanesulfonate, S-(trifluoromethyl)-2-cyclobutyl-6-n-propylbenzo[b]thiophenium tetrafluoroborate, S-(trifluoromethyl)-2-cyclopentyl-6-n-propylbenzo[b]thiophenium chloride, S-(trifluoromethyl)-2-cyclopentyl-6-n-propylbenzo[b]thiophenium bromide, S-(trifluoromethyl)-2-cyclopentyl-6-n-propylbenzo[b]thiophenium trifluoromethanesulfonate, S-(trifluoromethyl)-2-cyclopentyl-6-n-propylbenzo[b]thiophenium tetrafluoroborate, S-(trifluoromethyl)-2-cyclohexyl-6-n-propylbenzo[b]thiophenium chloride, S-(trifluoromethyl)-2-cyclohexyl-6-n-propylbenzo[b]thiophenium bromide, S-(trifluoromethyl)-2-cyclohexyl-6-n-propylbenzo[b]thiophenium trifluoromethanesulfonate, S-(trifluoromethyl)-2-cyclohexyl-6-n-propylbenzo[b]thiophenium tetrafluoroborate, S-(trifluoromethyl)-2-cycloheptyl-6-n-propylbenzo[b]thiophenium chloride, S-(trifluoromethyl)-2-cycloheptyl-6-n-propylbenzo[b]thiophenium bromide, S-(trifluoromethyl)-2-cycloheptyl-6-n-propylbenzo[b]thiophenium trifluoromethanesulfonate, S-(trifluoromethyl)-2-cycloheptyl-6-n-propylbenzo[b]thiophenium tetrafluoroborate, S-(trifluoromethyl)-2-methyl-6-iso-propylbenzo[b]thiophenium chloride, S-(trifluoromethyl)-2-methyl-6-iso-propylbenzo[b]thiophenium bromide, S-(trifluoromethyl)-2-methyl-6-iso-propylbenzo[b]thiophenium trifluoromethanesulfonate, S-(trifluoromethyl)-2-methyl-6-iso-propylbenzo[b]thiophenium tetrafluoroborate, S-(trifluoromethyl)-2-ethyl-6-iso-propylbenzo[b]thiophenium chloride, S-(trifluoromethyl)-2-ethyl-6-iso-propylbenzo[b]thiophenium bromide, S-(trifluoromethyl)-2-ethyl-6-iso-propylbenzo[b]thiophenium trifluoromethanesulfonate, S-(trifluoromethyl)-2-ethyl-6-iso-propylbenzo[b]thiophenium tetrafluoroborate, S-(trifluoromethyl)-2-n-propyl-6-iso-propylbenzo[b]thiophenium chloride, S-(trifluoromethyl)-2-n-propyl-6-iso-propylbenzo[b]thiophenium bromide, S-(trifluoromethyl)-2-n-propyl-5-iso-propylbenzo[b]thiophenium trifluoromethanesulfonate, S-(trifluoromethyl)-2-n-propyl-6-iso-propylbenzo[b]thiophenium tetrafluoroborate, S-(trifluoromethyl)-2-iso-propyl-6-iso-propylbenzo[b]thiophenium chloride, S-(trifluoromethyl)-2-iso-propyl-6-iso-propylbenzo[b]thiophenium bromide, S-(trifluoromethyl)-2-iso-propyl-6-iso-propylbenzo[b]thiophenium trifluoromethanesulfonate, S-(trifluoromethyl)-2-iso-propyl-6-iso-propylbenzo[b]thiophenium tetrafluoroborate, S-(trifluoromethyl)-2-n-butyl-6-iso-propylbenzo[b]thiophenium chloride, S-(trifluoromethyl)-2-n-butyl-6-iso-propylbenzo[b]thiophenium bromide, S-(trifluoromethyl)-2-n-butyl-6-iso-propylbenzo[b]thiophenium trifluoromethanesulfonate, S-(trifluoromethyl)-2-n-butyl-6-iso-propylbenzo[b]thiophenium tetrafluoroborate, S-(trifluoromethyl)-2-tert-butyl-6-iso-propylbenzo[b]thiophenium chloride, S-(trifluoromethyl)-2-tert-butyl-6-iso-propylbenzo[b]thiophenium bromide, S-(trifluoromethyl)-2-tert-butyl-6-iso-propylbenzo[b]thiophenium trifluoromethanesulfonate, S-(trifluoromethyl)-2-tert-butyl-6-iso-propylbenzo[b]thiophenium tetrafluoroborate, S-(trifluoromethyl)-2-cyclopropyl-6-iso-propylbenzo[b]thiophenium chloride, S-(trifluoromethyl)-2-cyclopropyl-6-iso-propylbenzo[b]thiophenium bromide, S-(trifluoromethyl)-2-cyclopropyl-6-iso-propylbenzo[b]thiophenium trifluoromethanesulfonate, S-(trifluoromethyl)-2-cyclopropyl-6-iso-propylbenzo[b]thiophenium tetrafluoroborate, S-(trifluoromethyl)-2-cyclobutyl-6-iso-propylbenzo[b]thiophenium chloride, S-(trifluoromethyl)-2-cyclobutyl-6-iso-propylbenzo[b]thiophenium bromide, S-(trifluoromethyl)-2-cyclobutyl-6-iso-propylbenzo[b]thiophenium trifluoromethanesulfonate, S-(trifluoromethyl)-2-cyclobutyl-6-iso-propylbenzo[b]thiophenium tetrafluoroborate, S-(trifluoromethyl)-2-cyclopentyl-6-iso-propylbenzo[b]thiophenium chloride, S-(trifluoromethyl)-2-cyclopentyl-6-iso-propylbenzo[b]thiophenium bromide, S-(trifluoromethyl)-2-cyclopentyl-6-iso-propylbenzo[b]thiophenium trifluoromethanesulfonate, S-(trifluoromethyl)-2-cyclopentyl-6-iso-propylbenzo[b]thiophenium tetrafluoroborate, S-(trifluoromethyl)-2-cyclohexyl-6-iso-propylbenzo[b]thiophenium chloride, S-(trifluoromethyl)-2-cyclohexyl-6-iso-propylbenzo[b]thiophenium bromide, S-(trifluoromethyl)-2-cyclohexyl-6-iso-propylbenzo[b]thiophenium trifluoromethanesulfonate, S-(trifluoromethyl)-2-cyclohexyl-6-iso-propylbenzo[b]thiophenium tetrafluoroborate, S-(trifluoromethyl)-2-cycloheptyl-6-iso-propylbenzo[b]thiophenium chloride, S-(trifluoromethyl)-2-cycloheptyl-6-iso-propylbenzo[b]thiophenium bromide, S-(trifluoromethyl)-2-cycloheptyl-6-iso-propylbenzo[b]thiophenium trifluoromethanesulfonate, S-(trifluoromethyl)-2-cycloheptyl-6-iso-propylbenzo[b]thiophenium tetrafluoroborate, S-(trifluoromethyl)-2-methyl-6-tert-butylbenzo[b]thiophenium chloride, S-(trifluoromethyl)-2-methyl-6-tert-butylbenzo[b]thiophenium bromide, S-(trifluoromethyl)-2-methyl-6-tert-butylbenzo[b]thiophenium trifluoromethanesulfonate, S-(trifluoromethyl)-2-methyl-6-tert-butylbenzo[b]thiophenium tetrafluoroborate, S-(trifluoromethyl)-2-ethyl-6-tert-butylbenzo[b]thiophenium chloride, S-(trifluoromethyl)-2-ethyl-6-tert-butylbenzo[b]thiophenium bromide, S-(trifluoromethyl)-2-ethyl-6-tert-butylbenzo[b]thiophenium trifluoromethanesulfonate, S-(trifluoromethyl)-2-ethyl-6-tert-butylbenzo[b]thiophenium tetrafluoroborate, S-(trifluoromethyl)-2-n-propyl-6-tert-butylbenzo[b]thiophenium chloride, S-(trifluoromethyl)-2-n-propyl-6-tert-butylbenzo[b]thiophenium bromide, S-(trifluoromethyl)-2-n-propyl-5-tert-butylbenzo[b]thiophenium trifluoromethanesulfonate, S-(trifluoromethyl)-2-n-propyl-6-tert-butylbenzo[b]thiophenium tetrafluoroborate, S-(trifluoromethyl)-2-iso-propyl-6-tert-butylbenzo[b]thiophenium chloride, S-(trifluoromethyl)-2-iso-propyl-6-tert-butylbenzo[b]thiophenium bromide, S-(trifluoromethyl)-2-iso-propyl-6-tert-butylbenzo[b]thiophenium trifluoromethanesulfonate, S-(trifluoromethyl)-2-iso-propyl-6-tert-butylbenzo[b]thiophenium tetrafluoroborate, S-(trifluoromethyl)-2-n-butyl-6-tert-butylbenzo[b]thiophenium chloride, S-(trifluoromethyl)-2-n-butyl-6-tert-butylbenzo[b]thiophenium bromide, S-(trifluoromethyl)-2-n-butyl-6-tert-butylbenzo[b]thiophenium trifluoromethanesulfonate, S-(trifluoromethyl)-2-n-butyl-6-tert-butylbenzo[b]thiophenium tetrafluoroborate, S-(trifluoromethyl)-2-tert-butyl-6-tert-butylbenzo[b]thiophenium chloride, S-(trifluoromethyl)-2-tert-butyl-6-tert-butylbenzo[b]thiophenium chloride, S-(trifluoromethyl)-2-tert-butyl-6-tert-butylbenzo[b]thiophenium trifluoromethanesulfonate, S-(trifluoromethyl)-2-tert-butyl-6-tert-butylbenzo[b]thiophenium tetrafluoroborate, S-(trifluoromethyl)-2-cyclopropyl-6-tert-butylbenzo[b]thiophenium chloride, S-(trifluoromethyl)-2-cyclopropyl-6-tert-butylbenzo[b]thiophenium bromide, S-(trifluoromethyl)-2-cyclopropyl-6-tert-butylbenzo[b]thiophenium trifluoromethanesulfonate, S-(trifluoromethyl)-2-cyclopropyl-6-tert-butylbenzo[b]thiophenium tetrafluoroborate, S-(trifluoromethyl)-2-cyclobutyl-6-tert-butylbenzo[b]thiophenium chloride, S-(trifluoromethyl)-2-cyclobutyl-6-tert-butylbenzo[b]thiophenium bromide, q-(trifluoromethyl)-2-cyclobutyl-6-tert-butylbenzo[b]thiophenium trifluoromethanesulfonate, S-(trifluoromethyl)-2-cyclobutyl-6-tert-butylbenzo[b]thiophenium tetrafluoroborate, S-(trifluoromethyl)-2-cyclopentyl-6-tert-butylbenzo[b]thiophenium chloride, S-(trifluoromethyl)-2-cyclopentyl-6-tert-butylbenzo[b]thiophenium bromide, S-(trifluoromethyl)-2-cyclopentyl-6-tert-butylbenzo[b]thiophenium trifluoromethanesulfonate, S-(trifluoromethyl)-2-cyclopentyl-6-tert-butylbenzo[b]thiophenium tetrafluoroborate, S-(trifluoromethyl)-2-cyclohexyl-6-tert-butylbenzo[b]thiophenium chloride, S-(trifluoromethyl)-2-cyclohexyl-6-tert-butylbenzo[b]thiophenium bromide, S-(trifluoromethyl)-2-cyclohexyl-6-tert-butylbenzo[b]thiophenium trifluoromethanesulfonate, S-(trifluoromethyl)-2-cyclohexyl-6-tert-butylbenzo[b]thiophenium tetrafluoroborate, S-(trifluoromethyl)-2-cycloheptyl-6-tert-butylbenzo[b]thiophenium chloride, S-(trifluoromethyl)-2-cycloheptyl-6-tert-butylbenzo[b]thiophenium bromide, S-(trifluoromethyl)-2-cycloheptyl-6-tert-butylbenzo[b]thiophenium trifluoromethanesulfonate, S-(trifluoromethyl)-2-cycloheptyl-6-tert-butylbenzo[b]thiophenium tetrafluoroborate, S-(trifluoromethyl)-2-methyl-6-fluorobenzo[b]thiophenium chloride, S-(trifluoromethyl)-2-methyl-6-fluorobenzo[b]thiophenium bromide, S-(trifluoromethyl)-2-methyl-6-fluorobenzo[b]thiophenium trifluoromethanesulfonate, S-(trifluoromethyl)-2-methyl-6-fluorobenzo[b]thiophenium tetrafluoroborate, S-(trifluoromethyl)-2-ethyl-6-fluorobenzo[b]thiophenium chloride, S-(trifluoromethyl)-2-ethyl-6-fluorobenzo[b]thiophenium bromide, S-(trifluoromethyl)-2-ethyl-6-fluorobenzo[b]thiophenium trifluoromethanesulfonate, S-(trifluoromethyl)-2-ethyl-6-fluorobenzo[b]thiophenium tetrafluoroborate, S-(trifluoromethyl)-2-n-propyl-6-fluorobenzo[b]thiophenium chloride, S-(trifluoromethyl)-2-n-propyl-6-fluorobenzo[b]thiophenium bromide, S-(trifluoromethyl)-2-n-propyl-5-fluorobenzo[b]thiophenium trifluoromethanesulfonate, S-(trifluoromethyl)-2-n-propyl-6-fluorobenzo[b]thiophenium tetrafluoroborate, S-(trifluoromethyl)-2-iso-propyl-6-fluorobenzo[b]thiophenium chloride, S-(trifluoromethyl)-2-iso-propyl-6-fluorobenzo[b]thiophenium bromide, S-(trifluoromethyl)-2-iso-propyl-6-fluorobenzo[b]thiophenium trifluoromethanesulfonate, S-(trifluoromethyl)-2-iso-propyl-6-fluorobenzo[b]thiophenium tetrafluoroborate, S-(trifluoromethyl)-2-n-butyl-6-fluorobenzo[b]thiophenium chloride, S-(trifluoromethyl)-2-n-butyl-6-fluorobenzo[b]thiophenium bromide, S-(trifluoromethyl)-2-n-butyl-6-n-propylbenzo[b]thiophenium trifluoromethanesulfonate, S-(trifluoromethyl)-2-n-butyl-6-fluorobenzo[b]thiophenium tetrafluoroborate, S-(trifluoromethyl)-2-tert-butyl-6-fluorobenzo[b]thiophenium chloride, S-(trifluoromethyl)-2-tert-butyl-6-fluorobenzo[b]thiophenium bromide, S-(trifluoromethyl)-2-tert-butyl-6-fluorobenzo[b]thiophenium trifluoromethanesulfonate, S-(trifluoromethyl)-2-tert-butyl-6-fluorobenzo[b]thiophenium tetrafluoroborate, S-(trifluoromethyl)-2-cyclopropyl-6-fluorobenzo[b]thiophenium chloride, S-(trifluoromethyl)-2-cyclopropyl-6-fluorobenzo[b]thiophenium bromide, S-(trifluoromethyl)-2-cyclopropyl-6-fluorobenzo[b]thiophenium trifluoromethanesulfonate, S-(trifluoromethyl)-2-cyclopropyl-6-fluorobenzo[b]thiophenium tetrafluoroborate, S-(trifluoromethyl)-2-cyclobutyl-6-fluorobenzo[b]thiophenium chloride, S-(trifluoromethyl)-2-cyclobutyl-6-fluorobenzo[b]thiophenium bromide, S-(trifluoromethyl)-2-cyclobutyl-6-fluorobenzo[b]thiophenium trifluoromethanesulfonate, S-(trifluoromethyl)-2-cyclobutyl-6-fluorobenzo[b]thiophenium tetrafluoroborate, S-(trifluoromethyl)-2-cyclopentyl-6-fluorobenzo[b]thiophenium chloride, S-(trifluoromethyl)-2-cyclopentyl-6-fluorobenzo[b]thiophenium bromide, S-(trifluoromethyl)-2-cyclopentyl-6-fluorobenzo[b]thiophenium trifluoromethanesulfonate, S-(trifluoromethyl)-2-cyclopentyl-6-fluorobenzo[b]thiophenium tetrafluoroborate, S-(trifluoromethyl)-2-cyclohexyl-6-fluorobenzo[b]thiophenium chloride, S-(trifluoromethyl)-2-cyclohexyl-6-fluorobenzo[b]thiophenium bromide, S-(trifluoromethyl)-2-cyclohexyl-6-fluorobenzo[b]thiophenium trifluoromethanesulfonate, S-(trifluoromethyl)-2-cyclohexyl-6-fluorobenzo[b]thiophenium tetrafluoroborate, S-(trifluoromethyl)-2-cycloheptyl-6-fluorobenzo[b]thiophenium chloride, S-(trifluoromethyl)-2-cycloheptyl-6-fluorobenzo[b]thiophenium bromide, S-(trifluoromethyl)-2-cycloheptyl-6-fluorobenzo[b]thiophenium trifluoromethanesulfonate, S-(trifluoromethyl)-2-cycloheptyl-6-fluorobenzo[b]thiophenium tetrafluoroborate, S-(trifluoromethyl)-2-methyl-6-chlorobenzo[b]thiophenium chloride, S-(trifluoromethyl)-2-methyl-6-chlorobenzo[b]thiophenium bromide, S-(trifluoromethyl)-2-methyl-6-chlorobenzo[b]thiophenium trifluoromethanesulfonate, S-(trifluoromethyl)-2-methyl-6-chlorobenzo[b]thiophenium tetrafluoroborate, S-(trifluoromethyl)-2-ethyl-6-chlorobenzo[b]thiophenium chloride, S-(trifluoromethyl)-2-ethyl-6-chlorobenzo[b]thiophenium bromide, S-(trifluoromethyl)-2-ethyl-6-chlorobenzo[b]thiophenium trifluoromethanesulfonate, S-(trifluoromethyl)-2-ethyl-6-chlorobenzo[b]thiophenium tetrafluoroborate, S-(trifluoromethyl)-2-n-propyl-6-chlorobenzo[b]thiophenium chloride, S-(trifluoromethyl)-2-n-propyl-6-chlorobenzo[b]thiophenium bromide, S-(trifluoromethyl)-2-n-propyl-5-chlorobenzo[b]thiophenium trifluoromethanesulfonate, S-(trifluoromethyl)-2-n-propyl-6-chlorobenzo[b]thiophenium tetrafluoroborate, S-(trifluoromethyl)-2-iso-propyl-6-chlorobenzo[b]thiophenium chloride, S-(trifluoromethyl)-2-iso-propyl-6-chlorobenzo[b]thiophenium bromide, S-(trifluoromethyl)-2-iso-propyl-6-chlorobenzo[b]thiophenium trifluoromethanesulfonate, S-(trifluoromethyl)-2-iso-propyl-6-chlorobenzo[b]thiophenium tetrafluoroborate, S-(trifluoromethyl)-2-n-butyl-6-chlorobenzo[b]thiophenium chloride, S-(trifluoromethyl)-2-n-butyl-6-chlorobenzo[b]thiophenium bromide, S-(trifluoromethyl)-2-n-butyl-6-n-propylbenzo[b]thiophenium trifluoromethanesulfonate, S-(trifluoromethyl)-2-n-butyl-6-chlorobenzo[b]thiophenium tetrafluoroborate, S-(trifluoromethyl)-2-tert-butyl-6-chlorobenzo[b]thiophenium chloride, S-(trifluoromethyl)-2-tert-butyl-6-chlorobenzo[b]thiophenium bromide, S-(trifluoromethyl)-2-tert-butyl-6-chlorobenzo[b]thiophenium trifluoromethanesulfonate, S-(trifluoromethyl)-2-tert-butyl-6-chlorobenzo[b]thiophenium tetrafluoroborate, S-(trifluoromethyl)-2-cyclopropyl-6-chlorobenzo[b]thiophenium chloride, S-(trifluoromethyl)-2-cyclopropyl-6-chlorobenzo[b]thiophenium bromide, S-(trifluoromethyl)-2-cyclopropyl-6-chlorobenzo[b]thiophenium trifluoromethanesulfonate, S-(trifluoromethyl)-2-cyclopropyl-6-chlorobenzo[b]thiophenium tetrafluoroborate, S-(trifluoromethyl)-2-cyclobutyl-6-chlorobenzo[b]thiophenium chloride, S-(trifluoromethyl)-2-cyclobutyl-6-chlorobenzo[b]thiophenium bromide, S-(trifluoromethyl)-2-cyclobutyl-6-chlorobenzo[b]thiophenium trifluoromethanesulfonate, S-(trifluoromethyl)-2-cyclobutyl-6-chlorobenzo[b]thiophenium tetrafluoroborate, S-(trifluoromethyl)-2-cyclopentyl-6-chlorobenzo[b]thiophenium chloride, S-(trifluoromethyl)-2-cyclopentyl-6-chlorobenzo[b]thiophenium bromide, S-(trifluoromethyl)-2-cyclopentyl-6-chlorobenzo[b]thiophenium trifluoromethanesulfonate, S-(trifluoromethyl)-2-cyclopentyl-6-chlorobenzo[b]thiophenium tetrafluoroborate, S-(trifluoromethyl)-2-cyclohexyl-6-chlorobenzo[b]thiophenium chloride, S-(trifluoromethyl)-2-cyclohexyl-6-chlorobenzo[b]thiophenium bromide, S-(trifluoromethyl)-2-cyclohexyl-6-chlorobenzo[b]thiophenium trifluoromethanesulfonate, S-(trifluoromethyl)-2-cyclohexyl-6-chlorobenzo[b]thiophenium tetrafluoroborate, S-(trifluoromethyl)-2-cycloheptyl-6-chlorobenzo[b]thiophenium chloride, S-(trifluoromethyl)-2-cycloheptyl-6-chlorobenzo[b]thiophenium bromide, S-(trifluoromethyl)-2-cycloheptyl-6-chlorobenzo[b]thiophenium trifluoromethanesulfonate, S-(trifluoromethyl)-2-cycloheptyl-6-chlorobenzo[b]thiophenium tetrafluoroborate, S-(trifluoromethyl)-2-phenylbenzo[b]thiophenium chloride, S-(trifluoromethyl)-2-phenylbenzo[b]thiophenium bromide, S-(trifluoromethyl)-2-phenylbenzo[b]thiophenium trifluoromethanesulfonate, S-(trifluoromethyl)-2-phenylbenzo[b]thiophenium tetrafluoroborate, S-(trifluoromethyl)-2-(4-methylphenyl)benzo[b]thiophenium chloride, S-(trifluoromethyl)-2-(4-methylphenyl)benzo[b]thiophenium bromide, S-(trifluoromethyl)-2-(4-methylphenyl)benzo[b]thiophenium trifluoromethanesulfonate, S-(trifluoromethyl)-2-(4-methylphenyl)benzo[b]thiophenium tetrafluoroborate, S-(trifluoromethyl)-2-(4-chlorophenyl)benzo[b]thiophenium chloride, S-(trifluoromethyl)-2-(4-chlorophenyl)benzo[b]thiophenium bromide, S-(trifluoromethyl)-2-(4-chlorophenyl)benzo[b]thiophenium trifluoromethanesulfonate, S-(trifluoromethyl)-2-(4-chlorophenyl)benzo[b]thiophenium tetrafluoroborate, S-(trifluoromethyl)-2-(4-bromophenyl)benzo[b]thiophenium chloride, S-(trifluoromethyl)-2-(4-bromophenyl)benzo[b]thiophenium bromide, S-(trifluoromethyl)-2-(4-bromophenyl)benzo[b]thiophenium trifluoromethanesulfonate, S-(trifluoromethyl)-2-(4-bromophenyl)benzo[b]thiophenium tetrafluoroborate, and the like. Preferable examples include S-(trifluoromethyl)-2-cyclopropyl-benzo[b]thiophenium trifluoromethanesulfonate, S-(trifluoromethyl)-2-cyclopropyl-benzo[b]thiophenium tetrafluoroborate, S-(trifluoromethyl)-2-cyclobutyl-benzo[b]thiophenium trifluoromethanesulfonate, S-(trifluoromethyl)-2-cyclobutyl-benzo[b]thiophenium tetrafluoroborate, S-(trifluoromethyl)-2-cycloheptyl-benzo[b]thiophenium trifluoromethanesulfonate, S-(trifluoromethyl)-2-cyclopentyl-benzo[b]thiophenium tetrafluoroborate, S-(trifluoromethyl)-2-cyclohexyl-benzo[b]thiophenium trifluoromethanesulfonate, S-(trifluoromethyl)-2-cyclohexyl-benzo[b]thiophenium tetrafluoroborate, S-(trifluoromethyl)-2-cycloheptyl-benzo[b]thiophenium trifluoromethanesulfonate, S-(trifluoromethyl)-2-cycloheptyl-benzo[b]thiophenium tetrafluoroborate, S-(trifluoromethyl)-2-phenylbenzo[b]thiophenium chloride, S-(trifluoromethyl)-2-phenylbenzo[b]thiophenium bromide, S-(trifluoromethyl)-2-phenylbenzo[b]thiophenium trifluoromethanesulfonate, and S-(trifluoromethyl)-2-phenylbenzo[b]thiophenium tetrafluoroborate. Examples that are more preferable include S-(trifluoromethyl)-2-cyclopropyl-benzo[b]thiophenium trifluoromethanesulfonate, S-(trifluoromethyl)-2-cyclopropyl-benzo[b]thiophenium tetrafluoroborate, and S-(trifluoromethyl)-2-phenylbenzo[b]thiophenium tetrafluoroborate.

The S-(trifluoromethyl)-benzo[b]thiophenium derivative salt represented by the general formula (1) in the present invention can be produced by mixing the (trifluoromethyl)-(2-ethynylphenyl)sulfide derivative represented by the general formula (2) which corresponds to the derivative salt and an acid in an organic solvent at −40° C. or lower to conduct reaction in a temperature range of −40 to 50° C. for 1 to 24 hours.

Specific examples of the (trifluoromethyl)-(2-ethynylphenyl)sulfide derivative of the present invention represented by the general formula (2) include (trifluoromethyl)-[2-(1-propynyl)phenyl]sulfide, (trifluoromethyl)-[2-(1-n-butynyl)phenyl]sulfide, (trifluoromethyl)-[2-(1-n-pentynyl)phenyl]sulfide, (trifluoromethyl)-[2-(3-methyl-1-butynyl)phenyl]sulfide, (trifluoromethyl)-[2-(1-n-hexynyl)phenyl]sulfide, (trifluoromethyl)-[2-(3,3-dimethyl-1-butynyl)phenyl]sulfide, (trifluoromethyl)-[(2-cyclopropylethynyl)phenyl]sulfide, (trifluoromethyl)-[(2-cyclobutylethynyl)phenyl]sulfide, (trifluoromethyl)-[(2-cyclopentylethynyl)phenyl]sulfide, (trifluoromethyl)-[(2-cyclohexylethynyl)phenyl]sulfide, (trifluoromethyl)-[(2-cycloheptylethynyl)phenyl]sulfide, (trifluoromethyl)-[2-(1-propynyl)-3-methylphenyl]sulfide, (trifluoromethyl)-[2-(1-n-butynyl)-3-methylphenyl]sulfide, (trifluoromethyl)-[2-(1-n-pentynyl)-3-methylphenyl]sulfide, (trifluoromethyl)-[2-(3-methyl-1-butynyl)-3-methylphenyl]sulfide, (trifluoromethyl)-[2-(1-n-hexynyl)-3-methylphenyl]sulfide, (trifluoromethyl)-[2-(3,3-dimethyl-1-butynyl)-3-methylphenyl]sulfide, (trifluoromethyl)-[2-(2-cyclopropylethynyl)-3-methylphenyl]sulfide, (trifluoromethyl)-[2-(2-cyclobutylethynyl)-3-methylphenyl]sulfide, (trifluoromethyl)-[2-(2-cyclopentylethynyl)-6-methylphenyl]sulfide, (trifluoromethyl)-[2-(2-cyclohexylethynyl)-3-methylphenyl]sulfide, (trifluoromethyl)-[2-(2-cycloheptylethynyl)-3-methylphenyl]sulfide, (trifluoromethyl)-[2-(1-propenyl)-4-methylphenyl]sulfide, (trifluoromethyl)-[2-(1-n-butenyl)-4-methylphenyl]sulfide, (trifluoromethyl)-[2-(1-n-pentenyl)-4-methylphenyl]sulfide, (trifluoromethyl)-[2-(3-methyl-1-butenyl)-4-methylphenyl]sulfide, (trifluoromethyl)-[2-(1-n-hexynyl)-4-methylphenyl]sulfide, (trifluoromethyl)-[2-(3,3-dimethyl-1-butynyl)-4-methylphenyl]sulfide, (trifluoromethyl)-[2-(2-cyclopropylethynyl)-4-methylphenyl]sulfide, (trifluoromethyl)-[2-(2-cyclobutylethynyl)-4-methylphenyl]sulfide, (trifluoromethyl)-[2-(2-cyclopentylethynyl)-4-methylphenyl]sulfide, (trifluoromethyl)-[2-(2-cyclohexylethynyl)-4-methylphenyl]sulfide, (trifluoromethyl)-[2-(2-cycloheptylethynyl)-4-methylphenyl]sulfide, (trifluoromethyl)-[2-(1-propynyl)-5-methylphenyl]sulfide, (trifluoromethyl)-[2-(1-n-butynyl)-5-methylphenyl]sulfide, (trifluoromethyl)-[2-(1-n-pentynyl)-5-methylphenyl]sulfide, (trifluoromethyl)-[2-(3-methyl-1-propynyl)-5-methylphenyl]sulfide, (trifluoromethyl)-[2-(1-n-hexynyl)-5-methylphenyl]sulfide, (trifluoromethyl)-[2-(3,3-dimethyl-1-butynyl)-5-methylphenyl]sulfide, (trifluoromethyl)-[2-(2-cyclopropylethynyl)-5-methylphenyl]sulfide, (trifluoromethyl)-[2-(2-cyclobutylethynyl)-5-methylphenyl]sulfide, (trifluoromethyl)-[2-(2-cyclopentylethynyl)-5-methylphenyl]sulfide, (trifluoromethyl)-[2-(2-cyclohexylethynyl)-5-methylphenyl]sulfide, (trifluoromethyl)-[2-(2-cycloheptylethynyl)-5-methylphenyl]sulfide, (trifluoromethyl)-[2-(1-propynyl)-3-ethylphenyl]sulfide, (trifluoromethyl)-[2-(1-n-butynyl)-3-ethylphenyl]sulfide, (trifluoromethyl)-[2-(1-n-pentynyl)-3-ethylphenyl]sulfide, (trifluoromethyl)-[2-(3-methyl-1-butynyl)-3-ethylphenyl]sulfide, (trifluoromethyl)-[2-(1-n-hexynyl)-3-ethylphenyl]sulfide, (trifluoromethyl)-[2-(3,3-dimethyl-1-butynyl)-3-ethylphenyl]sulfide, (trifluoromethyl)-[2-(2- cyclopropylethynyl)-3-ethylphenyl]sulfide, (trifluoromethyl)-[2-(2-cyclobutylethynyl)-3-ethylphenyl]sulfide, (trifluoromethyl)-[2-(2-cyclopentylethynyl)-3-ethylphenyl]sulfide, (trifluoromethyl)-[2-(2-cyclohexylethynyl)-3-ethylphenyl]sulfide, (trifluoromethyl)-[2-(2-cycloheptylethynyl)-3-ethylphenyl]sulfide, (trifluoromethyl)-[2-(1-propynyl)-4-ethylphenyl]sulfide, (trifluoromethyl)-[2-(1-n-butynyl)-4-ethylphenyl]sulfide, (trifluoromethyl)-[2-(1-n-pentynyl)-4-ethylphenyl]sulfide, (trifluoromethyl)-[2-(3-methyl-1-butynyl)-4-ethylphenyl]sulfide, (trifluoromethyl)-[2-(1-n-hexynyl)-4-ethylphenyl]sulfide, (trifluoromethyl)-[2-(3,3-dimethyl-1-butynyl)-4-ethylphenyl]sulfide, (trifluoromethyl)-[2-(2-cyclopropylethynyl)-4-ethylphenyl]sulfide, (trifluoromethyl)-[2-(2-cyclobutylethynyl)-4-ethylphenyl]sulfide, (trifluoromethyl)-[2-(2-cyclopentylethynyl)-4-ethylphenyl]sulfide, (trifluoromethyl)-[2-(2-cyclohexylethynyl)-4-ethylphenyl]sulfide, (trifluoromethyl)-[2-(2-cycloheptylethynyl)-4-ethylphenyl]sulfide, (trifluoromethyl)-[2-(1-propynyl)-5-ethylphenyl]sulfide, (trifluoromethyl)-[2-(1-n-butynyl)-5-ethylphenyl]sulfide, (trifluoromethyl)-[2-(1-n-pentynyl)-5-ethylphenyl]sulfide, (trifluoromethyl)-[2-(3-methyl-1-butynyl)-5-ethylphenyl]sulfide, (trifluoromethyl)-[2-(1-n-hexynyl)-5-ethylphenyl]sulfide, (trifluoromethyl)-[2-(3,3-dimethyl-1-butynyl)-5-ethylphenyl]sulfide, (trifluoromethyl)-[2-(2-cyclopropylethynyl)-5-ethylphenyl]sulfide, (trifluoromethyl)-[2-(2-cyclobutylethynyl)-5-ethylphenyl]sulfide, (trifluoromethyl)-[2-(2-cyclopentylethynyl)-5-ethylphenyl]sulfide, (trifluoromethyl)-[2-(2-cyclohexylethynyl)-5-ethylphenyl]sulfide, (trifluoromethyl)-[2-(2-cycloheptylethynyl)-5-ethylphenyl]sulfide, (trifluoromethyl)-[2-(1-propynyl)-5-n-propylphenyl]sulfide, (trifluoromethyl)-[2-(1-n-butynyl)-5-n-propylphenyl]sulfide, (trifluoromethyl)-[2-(1-n-pentynyl)-5-n-propylphenyl]sulfide, (trifluoromethyl)-[2-(3-methyl-1-butynyl)-5-n-propylphenyl]sulfide, (trifluoromethyl)-[2-(1-n-hexynyl)-5-n-propylphenyl]sulfide, (trifluoromethyl)-[2-(3,3-dimethyl-1-butynyl)-5-n-propylphenyl]sulfide, (trifluoromethyl)-[2-(2-cyclopropylethynyl)-5-n-propylphenyl]sulfide, (trifluoromethyl)-[2-(2-cyclobutylethynyl)-5-n-propylphenyl]sulfide, (trifluoromethyl)-[2-(2-cyclopentylethynyl)-5-n-propylphenyl]sulfide, (trifluoromethyl)-[2-(2-cyclohexylethynyl)-6-n-propylphenyl]sulfide, (trifluoromethyl)-[2-(2-cycloheptylethynyl)-5-n-propylphenyl]sulfide, (trifluoromethyl)-[2-(1-propynyl)-5-iso-propylphenyl]sulfide, (trifluoromethyl)-[2-(1-n-butynyl)-5-iso-propylphenyl]sulfide, (trifluoromethyl)-[2-(1-n-pentynyl)-5-iso-propylphenyl]sulfide, (trifluoromethyl)-[2-(3-methyl-1-butynyl)-5-iso-propylphenyl]sulfide, (trifluoromethyl)-[2-(1-n-hexynyl)-5-iso-propylphenyl]sulfide, (trifluoromethyl)-[2-(3,3-dimethyl-1-butynyl)-5-iso-propylphenyl]sulfide, (trifluoromethyl)-[2-(2-cyclopropylethynyl)-5-iso-propylphenyl]sulfide, (trifluoromethyl)-[2-(2-cyclobutylethynyl)-5-iso-propylphenyl]sulfide, (trifluoromethyl)-[2-(2-cyclopentylethynyl)-5-iso-propylphenyl]sulfide, (trifluoromethyl)-[2-(2-cyclohexylethynyl)-5-iso-propylphenyl]sulfide, (trifluoromethyl)-[2-(2-cycloheptylethynyl)-5-iso-propylphenyl]sulfide, (trifluoromethyl)-[2-(1-propynyl)-5-tert-butylphenyl]sulfide, (trifluoromethyl)-[2-(1-n-butynyl)-5-tert-butylphenyl]sulfide, (trifluoromethyl)-[2-(1-n-pentynyl)-5-tert-butylphenyl]sulfide, (trifluoromethyl)-[2-(3-methyl-1-butynyl)-5-tert-butylphenyl]sulfide, (trifluoromethyl)-[2-(1-n-hexynyl)-5-tert-butylphenyl]sulfide, (trifluoromethyl)-[2-(3,3-dimethyl-1-butynyl)-5-tert-butylphenyl]sulfide, (trifluoromethyl)-[2-(2-cyclopropylethynyl)-5-tert-butylphenyl]sulfide, (trifluoromethyl)-[2-(2-cyclobutylethynyl)-5-tert-butylphenyl]sulfide, (trifluoromethyl)-[2-(2-cyclopentylethynyl)-5-tert-butylphenyl]sulfide, (trifluoromethyl)-[2-(2-cyclohexylethynyl)-5-tert-butylphenyl]sulfide, (trifluoromethyl)-[2-(2-cycloheptylethynyl)-5-tert-butylphenyl]sulfide, (trifluoromethyl)-[2-(1-propynyl)-5-fluorophenyl]sulfide, (trifluoromethyl)-[2-(1-butynyl)-5-fluorophenyl]sulfide, (trifluoromethyl)-[2-(1-n-pentynyl)-5-fluorophenyl]sulfide, (trifluoromethyl)-[2-(3-methyl-1-butynyl)-5-fluorophenyl]sulfide, (trifluoromethyl)-[2-(1-n-hexynyl)-5-fluorophenyl]sulfide, (trifluoromethyl)-[2-(3,3-dimethyl-1-butynyl)-5-fluorophenyl]sulfide, (trifluoromethyl)-[2-(2-cyclopropylethynyl)-5-fluorophenyl]sulfide, (trifluoromethyl)-[2-(2-cyclobutylethynyl)-5-fluorophenyl]sulfide, (trifluoromethyl)-[2-(2-cyclopentylethynyl)-5-fluorophenyl]sulfide, (trifluoromethyl)-[2-(2-cyclohexylethynyl)-5-fluorophenyl]sulfide, (trifluoromethyl)-[2-(2-cycloheptylethynyl)-5-fluorophenyl]sulfide, (trifluoromethyl)-[2-(1-propynyl)-5-chlorophenyl]sulfide, (trifluoromethyl)-[2-(1-n-butynyl)-5-chlorophenyl]sulfide, (trifluoromethyl)-[2-(1-n-pentynyl)-5-chlorophenyl]sulfide, (trifluoromethyl)-[2-(3-methyl-1-butynyl)-5-chlorophenyl]sulfide, (trifluoromethyl)-[2-(1-n-hexynyl)-5-chlorophenyl]sulfide, (trifluoromethyl)-[2-(3,3-dimethyl-1-butynyl)-5-chlorophenyl]sulfide, (trifluoromethyl)-[2-(2-cyclopropylethynyl)-5-chlorophenyl]sulfide, (trifluoromethyl)-[2-(2-cyclobutylethynyl)-5-chlorophenyl]sulfide, (trifluoromethyl)-[2-(2-cyclopentylethynyl)-5-chlorophenyl]sulfide, (trifluoromethyl)-[2-(2-cyclohexylethynyl)-5-chlorophenyl]sulfide, (trifluoromethyl)-[2-(2-cycloheptylethynyl)-5-chlorophenyl]sulfide, (trifluoromethyl)-[2-(2-phenylethynyl)phenyl]sulfide, (trifluoromethyl)-{2-[2-(4-methylphenyl)ethynyl]phenyl}sulfide, (trifluoromethyl)-{2-[2-(4-chlorophenyl)ethynyl]phenyl}sulfide, (trifluoromethyl)-{2-[2-(4-bromophenyl)ethynyl]phenyl}sulfide, and the like. Preferable examples thereof include (trifluoromethyl)-[2-(2-cyclopropylethynyl)phenyl]sulfide, (trifluoromethyl)-[2-(2-cyclobutylethynyl)phenyl]sulfide, (trifluoromethyl)-[2-(2-cyclopentylethynyl)phenyl]sulfide, (trifluoromethyl)-[2-(2-cyclohexylethynyl)phenyl]sulfide, (trifluoromethyl)-[2-(2-cycloheptylethynyl)phenyl]sulfide, and (trifluoromethyl)-[2-(2-phenylethynyl)phenyl]sulfide. More preferable example is (trifluoromethyl)-[2-(2-cyclopropylethynyl)phenyl]sulfide.

Examples of acids applicable to the production of the S-(trifluoromethyl)-benzo[b]thiophenium derivative salt of the present invention represented by the general formula (1) include trifluoromethanesulfonic acid, tetrafluoroboric acid, hydrofluoric acid, hydrochloric acid, hydrobromic acid, and hydroiodic acid. Trifluoromethanesulfonic acid, and tetrafluoroboric acid are preferably used. The amount of the derivative salt used is within a range of 1.0 to 5 equivalents based on (trifluoromethyl)-(2-phenylethynyl)phenyl)sulfide derivative necessary for the reaction.

As an organic solvent applicable to the production of the S-(trifluoromethyl)-benzo[b]thiophenium derivative salt of the present invention represented by the general formula (1), any organic solvent which is inert to the reaction and does not solidify at −80° C. can be applied, and specific examples thereof include halogenated hydrocarbons such as chloroform and dichloromethane, and ethers such as diethyl ether and tetrahydrofuran. The amount of the solvent used is 2 to 100 times the weight of (trifluoromethyl)-(2-ethynylphenyl)sulfide derivative necessary for the reaction.

The method for producing the (trifluoromethyl)-(2-ethynylphenyl)sulfide derivative of the present invention represented by the general formula (2) is not particularly limited, and for example, the (trifluoromethyl)-(2-ethynylphenyl)sulfide derivative can be prepared by reaction of a corresponding (trifluoromethyl)-(2-iodophenyl)sulfide derivative and an acetylene derivative in the presence of palladium chloride or copper iodide.

The S-(trifluoromethyl)-benzo[b]thiophenium derivative salt of the present invention represented by the general formula (1) is useful as a trifluoromethylating agent.

Application of the trifluoromethylating agent of the present invention is not particularly limited, and examples thereof include esters, amides, malononitrile derivatives, aromatic thiols, and the like, which have a hydrogen atom capable of being eliminated by a base at an α position and can form anionic species.

Specific examples of the carboxylic acid derivative represented by the general formula (3) which can be applied to the trifluoromethylating agent of the present invention include ethyl acetate, ethyl propionate, ethyl butanoate, ethyl pentanoate, ethyl hexanoate, ethyl heptanoate, ethyl octanoate, ethyl nonanoate, ethyl decanoate, propyl acetate, propyl propionate, propyl butanoate, propyl pentanoate, propyl hexanoate, propyl heptanoate, propyl octanoate, propyl nonanoate, propyl decanoate, n-butyl acetate, n-butyl propionate, n-butyl butanoate, n-butyl pentanoate, n-butyl hexanoate, n-butylheptanoate, n-butyl octanoate, n-butyl nonanoate, n-butyl decanoate, tert-butyl acetate, tert-butyl propionate, tert-butyl butanoate, tert-butyl pentanoate, tert-butyl hexanoate, tert-butyl heptanoate, tert-butyl octanoate, tert-butyl nonanoate, tert-butyl decanoate, ethyl 2-methylpropionate, ethyl 2-methylbutanoate, ethyl 2-methylpentanoate, ethyl 2-methylhexanoate, ethyl 2-methylheptanoate, ethyl 2-methyloctanoate, ethyl 2-methylnonanoate, propyl 2-ethylbutanoate, propyl 2-ethylpentanoate, propyl 2-ethylhexanoate, propyl 2-ethylheptanoate, propyl octanoate, ethyl acetoacetate, ethyl propioacetate, ethyl butyroacetate, ethyl 2-acetopropionate, ethyl 2-propiopropionate, ethyl 2-butyropropionate, ethyl 2-acetopropionate, ethyl 2-propiopropionate, ethyl 2-butyropropionate, methyl 1-indanone-2-carboxylate, ethyl 1-indanone-2-carboxylate, tert-butyl 1-indanone-2-carboxylate, benzyl 1-indanone-2-carboxylate, N,N-dimethylacetamide, N,N-diethylacetamide, N,N-dimethylpropionamide, N,N-diethylpropionamide, N,N-dimethylbutanamide, N,N-diethylbutanamide, N,N-dimethylpentamide, N,N-diethylpentamide, N,N-dimethylhexanamide, N,N-diethylhexanamide, N,N-dimethylheptanamide, N,N-diethylheptanamide, N,N-dimethyloctanamide, N,N-diethyloctanamide, N,N-dimethylnonanamide, N,N-diethylnonanamide, N,N-dimethyldecanamide, N,N-diethyldecanamide, N,N-dimethyl-2-methylpropionamide, N,N-diethyl-2-methylpropionamide, N,N-dimethyl-2-methylbutanamide, N,N-diethyl-2-methylbutanamide, N,N-dimethyl-2-methylpentamide, N,N-diethyl-2-methylpentamide, N,N-dimethyl-2-methylhexanamide, N,N-diethyl-2-methylhexanamide, ethyl N,N-dimethyl-2-methylheptanoate, ethyl N,N-diethyl-2-methylheptanoate, N,N-dimethyl-2-methyloctanamide, N,N-diethyl-2-methyloctanamide, N,N-dimethyl-2-methylnonanamide, N,N-diethyl-2-methylnonanamide, N,N-dimethyl-2-ethylbutanamide, N,N-diethyl-2-ethylbutanamide, N,N-dimethyl-2-ethylpentamide, N,N-diethyl-2-ethylpentamide, N,N-dimethylacetoacetamide, N,N-diethylacetoacetamide, N,N-dimethylpropioacetamide, N,N-diethylpropioacetamide, N,N-dimethylbutyroacetamide, N,N-diethylbutyroacetamide, N,N-dimethyl-2-acetopropionamide, N,N-diethyl-2-acetopropionamide, N,N-dimethyl-2-propiopropionamide, N,N-diethyl-2-propiopropionamide, N,N-dimethyl-2-butyropropionamide, N,N-diethyl-2-butyropropionamide, N,N-dimethyl-1-indanone-2-carboxamide, N,N-diethyl-1-indanone-2-carboxamide, and the like.

Specific examples of the α-trifluoromethylcarboxylic acid derivative represented by the general formula (4) which is obtained by trifluoromethylation of the carboxylic acid derivative of the present invention represented by the general formula (3) include ethyl 2-trifluoromethylacetate, ethyl 2-trifluoromethylpropionate, ethyl 2-trifluoromethylbutanoate, ethyl 2-trifluoromethylpentanoate, ethyl 2-trifluoromethylhexanoate, ethyl 2-trifluoromethylheptanoate, ethyl 2-trifluoromethyloctanoate, ethyl 2-trifluoromethylnonanoate, ethyl 2-trifluoromethyldecanoate, propyl 2-trifluoromethylacetate, propyl 2-trifluoromethylpropionate, propyl 2-trifluoromethylbutanoate, propyl 2-trifluoromethylpentanoate, propyl 2-trifluoromethylhexanoate, propyl 2-trifluoromethylheptanoate, propyl 2-trifluoromethyloctanoate, propyl 2-trifluoromethylnonanoate, propyl 2-trifluoromethyldecanoate, n-butyl 2-trifluoromethylacetate, n-butyl 2-trifluoromethylpropionate, n-butyl 2-trifluoromethylbutanoate, n-butyl 2-trifluoromethylpentanoate, n-butyl 2-trifluoromethylhexanoate, n-butyl 2-trifluoromethylheptanoate, n-butyl 2-trifluoromethyloctanoate, n-butyl 2-trifluoromethylnonanoate, n-butyl 2-trifluoromethyldecanoate, tert-butyl 2-trifluoromethylacetate, tert-butyl 2-trifluoromethylpropionate, tert-butyl 2-trifluoromethylbutanoate, tert-butyl 2-trifluoromethylpentanoate, tert-butyl 2-trifluoromethylhexanoate, tert-butyl 2-trifluoromethylheptanoate, tert-butyl 2-trifluoromethyloctanoate, tert-butyl 2-trifluoromethylnonanoate, tert-butyl 2-trifluoromethyldecanoate, ethyl 2-trifluoromethyl-2-methylpropionate, ethyl 2-trifluoromethyl-2-methylbutanoate, ethyl 2-trifluoromethyl-2-methylpentanoate, ethyl 2-trifluoromethyl-2-methylhexanoate, ethyl 2-trifluoromethyl-2-methylheptanoate, ethyl 2-trifluoromethyl-2-methyloctanoate, ethyl 2-trifluoromethyl-2-methylnonanoate, propyl 2-trifluoromethyl-2-ethylbutanoate, propyl 2-trifluoromethyl-2-ethylpentanoate, propyl 2-trifluoromethyl-2-ethylhexanoate, propyl 2-trifluoromethyl-2-ethylheptanoate, propyl 2-trifluoromethyloctanoate, ethyl 2-trifluoromethylacetoacetate, ethyl 2-trifluoromethylpropioacetate, ethyl 2-trifluoromethylbutyroacetate, ethyl 2-trifluoromethyl-2-acetopropionate, ethyl 2-trifluoromethyl-2-propiopropionate, ethyl 2-trifluoromethyl-2-butyropropionate, ethyl 2-trifluoromethyl-2-acetopropionate, ethyl 2-trifluoromethyl-2-propiopropionate, ethyl 2-trifluoromethyl-2-butyropropionate, methyl 2-trifluoromethyl-1-indanone-2-carboxylate, ethyl 2-trifluoromethyl-1-indanone-2-carboxylate, tert-butyl 2-trifluoromethyl-1-indanone-2-carboxylate, benzyl 2-trifluoromethyl-1-indanone-2-carboxylate, N,N-dimethyl-2-trifluoromethylacetamide, N,N-diethyl-2-trifluoromethylacetamide, N,N-dimethyl-2-trifluoromethylpropionamide, N,N-diethyl-2-trifluoromethylpropionamide, N,N-dimethyl-2-trifluoromethylbutanamide, N,N-diethyl-2-trifluoromethylbutanamide, N,N-dimethyl-2-trifluoromethylpentanamide, N,N-diethyl-2-trifluoromethylpentanamide, N,N-dimethyl-2-trifluoromethylhexanamide, N,N-diethyl-2-trifluoromethylhexanamide, N,N-dimethyl-2-trifluoromethylheptanamide, N,N-diethyl-2-trifluoromethylheptanamide, N,N-dimethyl-2-trifluoromethyloctanamide, N,N-diethyl-2-trifluoromethyloctanamide, N,N-dimethyl-2-trifluoromethylnonanamide, N,N-diethyl-2-trifluoromethylnonanamide, N,N-dimethyl-2- trifluoromethyldecanamide, N,N-diethyl-2-trifluoromethyldecanamide, N,N-dimethyl-2-trifluoromethyl-2-methylpropionamide, N,N-diethyl-2-trifluoromethyl-2-methylpropionamide, N,N-dimethyl-2-trifluoromethyl-2-methylbutanamide, N,N-diethyl-2-trifluoromethyl-2-methylbutanamide, N,N-dimethyl-2-trifluoromethyl-2-methylpentanamide, N,N-diethyl-2-trifluoromethyl-2-methylpentanamide, N,N-dimethyl-2-trifluoromethyl-2-methylhexanamide, N,N-diethyl-2-trifluoromethyl-2-methylhexanamide, N,N-dimethyl-2-trifluoromethyl-2-methylheptanamide, N,N-diethyl-2-trifluoromethyl-2-methylheptanamide, N,N-dimethyl-2-trifluoromethyl-2-methyloctanamide, N,N-diethyl-2-trifluoromethyl-2-methyloctanamide, N,N-dimethyl-2-trifluoromethyl-2-methylnonanamide, N,N-diethyl-2-trifluoromethyl-2-methylnonanamide, N,N-dimethyl-2-trifluoromethyl-2-ethylbutanamide, N,N-diethyl-2-trifluoromethyl-2-ethylbutanamide, N,N-dimethyl-2-trifluoromethyl-2-ethylpentanamide, N,N-diethyl-2-trifluoromethyl-2-ethylpentanamide, N,N-dimethyl-2-trifluoromethylacetoacetamide, N,N-diethyl-2-trifluoromethylacetoacetamide, N,N-dimethyl-2-trifluoromethylpropioacetamide, N,N-diethyl-2-trifluoromethylpropioacetamide, N,N-dimethyl-2-trifluoromethylbutyroacetamide, N,N-diethyl-2-trifluoromethylbutyroacetamide, N,N-dimethyl-2-trifluoromethyl-2-acetopropionamide, N,N-diethyl-2-trifluoromethyl-2-acetopropionamide, N,N-dimethyl-2-trifluoromethyl-2-propiopropionamide, N,N-diethyl-2-trifluoromethyl-2-propiopropionamide, N,N-dimethyl-2-trifluoromethyl-2-butyropropionamide, N,N-diethyl-2-trifluoromethyl-2-butyropropionamide, N,N-dimethyl-2-trifluoromethyl-1-indanone-2-carboxamide, N,N-diethyl-2-trifluoromethyl-1-indanone-2-carboxamide, and the like.

Specific examples of the malononitrile derivative represented by the general formula (5) which can be applied to the trifluoromethylating agent of the present invention include α-methylbenzylidenemalononitrile, α-ethylbenzylidenemalononitrile, 2-(2,3-dihydronaphthalen-4(1H)-ylidene)malononitrile, and the like.

Specific examples of the α-trifluoromethylated malononitrile derivative represented by the general formula (6) which is obtained by trifluoromethylation of the carboxylic acid derivative of the present invention represented by the general formula (5) include α-trifluoromethyl-α-methylbenzylidenemalononitrile, α-ethylbenzylidenemalononitrile, 2-(3-trifluoromethyl-2,3-dihydronaphthalen-4(1H)-ylidene)malononitrile, and the like.

A base available in the reaction for obtaining the α-trifluoromethylcarboxylic acid derivative represented by the general formula (4) and the α-trifluoromethylmalononitrile derivative represented by the general formula (6) using the trifluoromethylating agent of the present invention is not particularly limited, and specific examples thereof include sodium carbonate, potassium carbonate, triethylamine, 1,8-diazabicyclo[5.4.0]-7-undecene (hereinafter referred to as DBU), sodium hydride, potassium tert-butoxide, lithium diisopropylamide, lithium hexamethyldisilazide, n-butyllithium, phosphazene base such as tert-butylamino-tri(pyrrolodino)phosphorane (hereinafter referred to as $^1$P), and 1-ethyl-2,2,4,4,4-pentakis (dimethylamino)-2λ$^5$,4λ$^5$-catenadi(phosphazene) (hereinafter referred to as $^2$P), and the like, and the base is used in an amount of 1.0 to 2.0 equivalents based on a substrate necessary for the reaction.

A solvent available in the reaction for obtaining the α-trifluoromethylcarboxylic acid derivative represented by the general formula (4) and the α-trifluoromethylmalononitrile derivative represented by the general formula (6) using the trifluoromethylating agent of the present invention is not particularly limited as long as the solvent is inert to the reaction, and specific examples thereof include halogenated hydrocarbon solvents such as 1,2-dichloroethane, nitrile solvents such as acetonitrile, and propionitrile, ether solvents such as diethyl ether, di-iso-propyl ether, and tetrahydrofuran, aromatic hydrocarbon solvents such as benzene, toluene, and ethylbenzene, aprotic polar oil solvent such as N,N-dimethylformamide, N,N-dimethylacetamide, N-methylpyrrolidone, dimethyl sulfoxide, and the like, and the solvent is used in an amount 1.0 to 100 times the weight of the substrate necessary for the reaction.

The amount of trifluoromethylating agent used in the reaction for obtaining the α-trifluoromethylcarboxylic acid derivative represented by the general formula (4) and the α-trifluoromethylmalononitrile derivative represented by the general formula (6) using the trifluoromethylating agent of the present invention is 1.0 to 10 times the mole of the substrate necessary for the reaction.

Reaction temperature and time for the reaction for obtaining the α-trifluoromethylcarboxylic acid derivative represented by the general formula (4) and the α-trifluoromethylmalononitrile derivative represented by the general formula (6) using the trifluoromethylating agent of the present invention are different depending on difference of substrates and bases necessary for the reaction. The reaction is typically completed at a temperature range of −80 to 150° C. for 1 to 24 hours.

EXAMPLES

Hereinafter, the present invention will be described in detail with reference to Examples, but the present invention is not limited only to these examples.

Reference Example 1

Preparation of (trifluoromethyl)-(2-iodophenyl)sulfide

[Chemical formula 8]

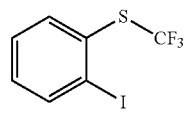

2-(trifluoromethylthio)benzenamine (1 g, 5.18 mmol) prepared in accordance with a method described in J. Fluorin. Chem. 1994, 69, 207 to 212, 5 ml of glacial acetic acid, and 3 ml of 50% sulfuric acid were added into a 50-ml eggplant flask equipped with a stirrer, and were dissolved. Then the mixture was cooled to 0° C. on an ice bath. To the mixture, 1 ml of an aqueous solution of sodium nitrite (0.43 g, 6.22 mmol) was added and the mixture was stirred for 1.5 hours. 1 ml of an aqueous solution of sodium iodide (0.95 g, 6.3 mmol) was added dropwise at 0° C. and the mixture was stirred for 30 minutes. After completion of the reaction, the reaction solution was gradually heated to room temperature and added to water, and the solution was extracted three times with ether. The obtained organic layer was washed three times with water, two times with a saturated sodium bisulfite aqueous solution, and three times with water, dried over anhydrous sodium sulfate, and concentrated to obtain a crude product.

The obtained crude product was purified by silica gel column chromatography (Hexane 100) to give target (trifluoromethyl)-(2-iodophenyl)sulfide (1.5 g, 95%) as a yellow oil.

$^1$H-NMR (200 MHz, CDCl$_3$) δ 7.98 (d, J=7.8 z, 1H), 7.79 (d, J=7.6 Hz, 1H), 7.39 (t, J=7.8 Hz, 1H), 7.11 (t, J=7.6 Hz, 1H) ppm.

$^{19}$F-NMR (188 MHz, CDCl$_3$) δ −42.3 (s) ppm.

Example 1

Preparation of 1-cyclopropylethynyl-2-trifluoromethylsulfanylbenzene

[Chemical formula 9]

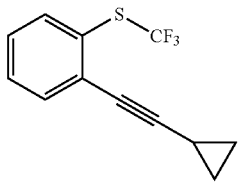

Bis(triphenylphosphine)palladium(II) dichloride ([(C$_6$H$_5$)$_3$ P]$_2$PdCl$_2$, 0.0518 g, 5 mol %), copper(I) iodide (0.0086 g, 3 mol %), and triethylamine (3 ml) were charged into a 25-ml round-bottomed flask equipped with a stirrer, and were suspended by stirring at room temperature. To the suspension, a solution obtained by dissolving 2-trifluoromethyl-sulfanyliodobenzene (1.08 g, 3.6 mmol) prepared in Reference Example 1 and cyclopropylacetylene (0.35 g, 5.3 mmol) in triethylamine (2 ml) was added dropwise, and the solution was stirred at room temperature overnight. After completion of the reaction, a solvent was removed under reduced pressure, and water was added to the obtained residue. The solution was extracted with ether, and the organic layers were combined together, washed with water, dried over magnesium sulfate, filtered, and concentrated to obtain a crude product. The obtained crude product was purified by silica gel column chromatography (hexane) to give target 1-cyclopropylethynyl-2-trifluoromethylsulfanylbenzene (0.67 g, yield: 78%) as an oil.

$^1$H-MMR (200 MHz, CDCl$_3$) δ: 0.81-0.97 (m, 4H), 1.43-1.56 (m, 1H), 7.21-7.39 (m, 2H), 7.45-7.49 (m, 1H), 7.61-7.65 (m, 1H).

$^{19}$F-MMR (188 Hz, CDCl$_3$) δ: −41.9 (s).

$^{13}$C-MMR (150 MHz, CDCl$_3$) δ: 136.5, 133.3, 131.9 (q, J=309 Hz, CF$_3$), 130.50, 130.46, 128.2, 127.9 (q, J=309 Hz, CF$_3$), 126.6, 100.5, 73.6, 9.1, 0.5.

Example 2

Preparation of 2-cyclopropyl-1-trifluoromethylbenzo[b]thiophenium triflate

[Chemical formula 10]

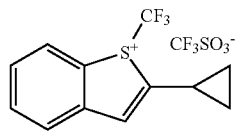

1-cyclopropylethynyl-2-trifluoromethylsulfanylbenzene (0.67 g, 2.77 mmol) prepared in Example 1 and anhydrous methylene chloride (5 ml) were charged into a 25-ml round-bottomed flask equipped with a stirrer, and cooled to −50° C. with stirring. To this mixture, trifluoromethanesulfonic acid (0.5 ml, 5.54 mmol) was added dropwise, and the solution was heated, and stirred at room temperature overnight. After completion of the reaction, a solvent was removed, ether (10 ml) was added to form a deposit, and the deposit was collected by filtration. The obtained crude product was dissolved in acetonitrile. After then, ether was added to form a precipitation, which was collected by filtration. This operation was repeated three times to purify the product. After the purification, target 2-cyclopropyl-1-trifluoromethylbenzo[b]thiophenyl triflate was obtained as a white solid (0.87 g, yield: 80%).

$^1$H-MMR (200 MHz, CD$_3$CM) δ: 1.03-1.31 (m, 5H), 7.76-7.97 (m, 4H), 8.29-8.36 (m, 1H).

$^{19}$F-MMR (188 MHz, CD$_3$CM) δ: −50.9 (s, 3F), −79.7 (s, 3F).

$^{13}$C-MMR (150 MHz, CDCl$_3$) δ: 145.6, 140.81, 140.79, 137.3, 132.4, 130.4, 128.8, 124.6, 124.4 (q, J=329 Hz, CF$_3$), 122.1 (q, J=321 Hz, CF$_3$), 11.8, 11.2, 10.0.

MS (ESI) m/z: 243 (M$^+$-CF$_3$SO$_3$).

Example 3

Preparation of methyl 1-oxo-2-trifluoromethylindane-2-carboxylate ester

Methyl 1-indanone-2-carboxylate (19 mg, 0.1 mmol), acetonitrile (1 ml), and 1,8-diazabicyclo[5.4.0]-7-undecene (DBU, 18 μl, 0.12 mmol) were charged into a 5-ml round-bottomed flask equipped with a stirrer, subjected to reaction at room temperature for 15 minutes, cooled to −43 to −45° C., and stirred for 5 minutes. To this solution, a solution of 2-cyclopropyl-1-trifluoromethylbenzo[b]thiophenyl triflate (58.8 mg, 0.15 mmol) prepared in Example 2 in acetonitrile (1 ml) was added dropwise over 15 minutes, and the mixture was stirred at the same temperature for 15 minutes. After completion of the reaction, the temperature was raised to room temperature, and a solvent was removed. The obtained residue was purified by silica gel column chromatography (benzene) to give target methyl 1-indanone-(2-trifluoromethyl)-2-carboxylate (23.7 mg, yield: 92%) as an oil.

Examples 4 to 17

Preparation of β-keto-α-trifluoromethylcarboxylic acid ester derivative

[Chemical formula 11]

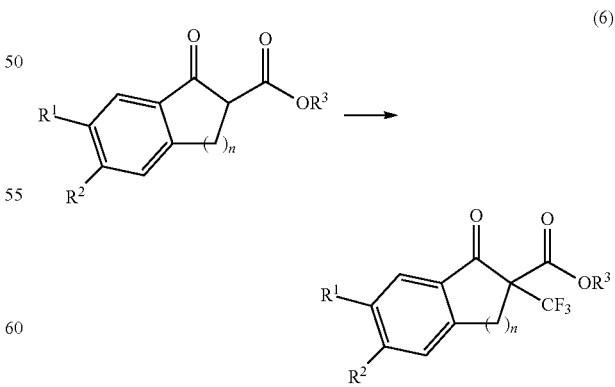

Reaction was conducted under conditions shown in Table 1 using β-ketocarboxylic acid ester derivatives represented by the above general formula (6) and shown in Table 1 instead of methyl 1-indanone-2-carboxylate used in Example 3. Results were shown in Table 1.

TABLE 1

| EXAMPLES | R¹ | R² | R³ | n = | SOLVENT | BASE (MOL) | REACTION TEMPERATURE | YIELD (%) |
|---|---|---|---|---|---|---|---|---|
| EXAMPLE 4 | H | H | Me | 1 | DICHLOROMETHANE | DBU (1.2) | ROOM TEMPERATURE | 82 |
| EXAMPLE 5 | H | H | Me | 1 | DICHLOROMETHANE | NEt3 (1.2) | ROOM TEMPERATURE | 17 |
| EXAMPLE 6 | H | H | Me | 1 | ACETONITRILE | DBU (1.2) | ROOM TEMPERATURE | 86 |
| EXAMPLE 7 | H | H | Me | 1 | THF | DBU (1.2) | ROOM TEMPERATURE | 87 |
| EXAMPLE 8 | H | H | Me | 1 | DICHLOROMETHANE | DBU (1.2) | −43~−45° C. | 76 |
| EXAMPLE 9 | H | H | Me | 1 | THF | DBU (1.2) | −43~−45° C. | 90 |
| EXAMPLE 10 | H | H | Me | 1 | ACETONITRILE | DBU (1.2) | −43~−45° C. | 92 |
| EXAMPLE 11 | H | H | CH₂Ph | 1 | ACETONITRILE | DBU (1.2) | −43~−45° C. | 90 |
| EXAMPLE 12 | H | H | t-Bu | 1 | ACETONITRILE | DBU (1.2) | −43~−45° C. | 78 |
| EXAMPLE 13 | H | Br | t-Bu | 1 | ACETONITRILE | DBU (1.2) | −43~−45° C. | 91 |
| EXAMPLE 14 | H | H | Me | 2 | ACETONITRILE | DBU (1.2) | −43~−45° C. | 47 |
| EXAMPLE 15 | H | Br | t-Bu | 1 | ACETONITRILE | DBU (2.0) | −43~−45° C. | 82 |
| EXAMPLE 16 | H | Br | t-Bu | 2 | ACETONITRILE | DBU (2.0) | −43~−45° C. | 95 |
| EXAMPLE 17 | H | OMe | Me | 2 | ACETONITRILE | DBU (2.0) | −43~−45° C. | 92 |

Example 18

Preparation of 2-trifluoromethyl-2-(methoxycarbonyl)cyclopentanone

Target 2-trifluoromethyl-2-(methoxycarbonyl)cyclopentanone (12.6 mg, yield: 60%) was obtained by using the same reaction instruments as in Example 3 and performing the same reaction operation as in Example 3 except that 2-(methoxycarbonyl)cyclopentanone was used instead of methyl 1-indanone-2-carboxylate, and 2 mol of DBU was used.

Examples 19 to 29

Preparation of β-keto-α-trifluoromethylcarboxylic acid ester derivative

[Chemical formula 12]

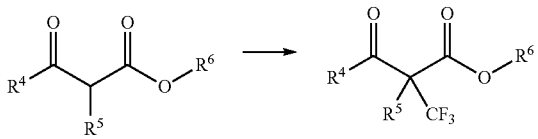

(7)

Reaction was conducted under conditions shown in Table 2 using β-ketocarboxylic acid ester derivatives represented by the above general formula (7) and shown in Table 12 instead of methyl 1-indanone-2-carboxylate used in Example 3. Results were shown in Table 2.

TABLE 2

| EXAMPLES | R⁴ | R⁵ | R⁶ | SOLVENT | BASE[1] (MOL) | REACTION TEMPERATURE | YIELD[2] (%) |
|---|---|---|---|---|---|---|---|
| EXAMPLE 19 | Et | Me | CH₂Ph | ACETONITRILE | ²P (1.2) | −43~−45° C. | (30) |
| EXAMPLE 20 | Et | Me | CH₂Ph | ACETONITRILE | ²P (2.0) | −43~−45° C. | 65 |
| EXAMPLE 21 | Et | Me | CH₂Ph | ACETONITRILE | ²P (2.0) | −43~−45° C. | 70 |
| EXAMPLE 22 | Et | Me | CH₂Ph | ACETONITRILE | ¹P (2.0) | −43~−45° C. | 84 |
| EXAMPLE 23 | Me | CH₂Ph | Et | ACETONITRILE | ¹P (2.0) | −43~−45° C. | 70 |
| EXAMPLE 24 | Me | Et | t-Bu | ACETONITRILE | ¹P (2.0) | −43~−45° C. | 68 (86) |
| EXAMPLE 25 | Ph | Me | Et | ACETONITRILE | ¹P (2.0) | −43~−45° C. | 87 |
| EXAMPLE 26 | Me | Et | Et | ACETONITRILE | ¹P (2.0) | −43~−45° C. | 44 (69) |

TABLE 2-continued

| EXAMPLES | $R^4$ | $R^5$ | $R^6$ | SOLVENT | BASE[1] (MOL) | REACTION TEMPERATURE | YIELD[2] (%) |
|---|---|---|---|---|---|---|---|
| EXAMPLE 27 | Ph | Et | Et | ACETONITRILE | $^1$P (2.0) | −43~−45° C. | 84 |
| EXAMPLE 28 | Ph | n-Pr | Et | ACETONITRILE | $^1$P (2.0) | −43~−45° C. | 71 |
| EXAMPLE 29 | n-Pr | CH$_2$Ph | Et | ACETONITRILE | $^1$P (2.0) | −43~−45° C. | 83 |

[1] $^1$P represents tert-butylamino-tri(pyrrolodino)phosphorane, and $^2$P represents 1-ethyl-2,2,4,4,4-pentakis(dimethylamino)-2$\lambda^5$, 4$\lambda^5$-catenadi(phosphazene).
[2] The quantitative value by $^{19}$F-NMR is shown in parentheses.

Examples 30 to 33

Preparation of 2-(3-trifluoromethyl)-2,3-dihydronaphthalen-4(1H)-ylidene)malononitrile

[Chemical formula 13]

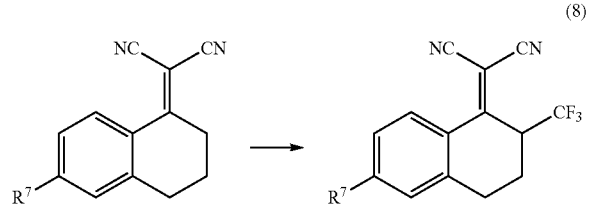

(8)

Reaction was conducted under conditions shown in Table 3 using malononitrile derivatives represented by the above general formula (8) and shown in Table 3 instead of methyl 1-indanone-2-carboxylate used in Example 3. Results were shown in Table 3.

TABLE 3

| EXAMPLES | R' | SOLVENT | BASE (MOL) | REACTION TEMPERATURE | YIELD (%) |
|---|---|---|---|---|---|
| EXAMPLE 30 | H | ACETONITRILE | DBU(1.2) | ROOM TEMPERATURE | 64 |
| EXAMPLE 31 | H | ACETONITRILE | DBU(1.2) | −43~−45° C. | 84 |
| EXAMPLE 32 | H | ACETONITRILE | $^1$P(1.2) | −43~−45° C. | 89 |
| EXAMPLE 33 | OMe | ACETONITRILE | $^1$P(1.2) | −43~−45° C. | 90 |

Examples 34 to 37 Preparation of 2-(3-(trifluoromethyl)-indaylidene)malononitrile

[Chemical formula 14]

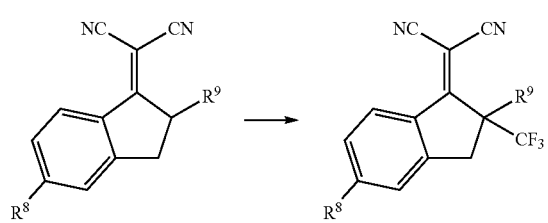

(9)

Reaction was conducted under conditions shown in Table 4 using malononitrile derivatives represented by the above general formula (9) and shown in Table 4 instead of methyl 1-indanone-2-carboxylate used in Example 3. Results were shown in Table 4.

TABLE 4

| EXAMPLES | $R^8$ | $R^9$ | SOLVENT | BASE (MOL) | REACTION TEMPERATURE | YIELD (%) |
|---|---|---|---|---|---|---|
| EXAMPLE 34 | H | Me | ACETONITRILE | DBU (1.2) | −43~−45° C. | 93 |
| EXAMPLE 35 | H | Me | ACETONITRILE | $^1$P (1.2) | −43~−45° C. | 75 |
| EXAMPLE 36 | Cl | Me | ACETONITRILE | DBU (1.2) | −43~−45° C. | 91 |
| EXAMPLE 37 | Cl | Me | ACETONITRILE | $^1$P (1.2) | −43~−45° C. | 74 |

Example 38

Preparation of 2-phenyl-1-trifluoromethylbenzo[b]thiophenium triflate

Preparation of (trifluoromethyl)-(2-iodophenyl)sulfide

[Chemical formula 15]

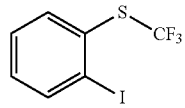

2-(trifluoromethylthio)benzenamine (1 g, 5.18 mmol) prepared in accordance with the method described in J. Fluorin. Chem. 1994, 69, 207 to 212, 5 ml of glacial acetic acid, and 3 ml of 50% sulfuric acid were charged into a 50-ml eggplant flask equipped with a stirrer, were dissolved, and then the mixture was cooled to 0° C. on an ice bath. To the mixture, 1 ml of an aqueous solution of sodium nitrite (0.43 g, 6.22 mmol) was added and the mixture was stirred for 1.5 hours. Then, 1 ml of an aqueous solution of sodium iodide (0.95 g, 6.3 mmol) was added dropwise at 0° C. and the mixture was stirred for 30 minutes. After completion of the reaction, the reaction solution was gradually heated to room temperature and added to water, and the solution was extracted three times with ether. The obtained organic layer was washed three times with water, two times with a saturated sodium bisulfite aqueous solution, and three times with water, dried over anhydrous sodium sulfate, and concentrated to obtain a crude product.

The obtained crude product was purified by silica gel column chromatography (Hexane 100) to give target (trifluoromethyl)(2-iodophenyl)sulfide (1.5 g, 95%) as a yellow oil.

$^1$H-NMR (200 MHz, CDCl$_3$) δ 7.98 (d, J=7.8 z, 1H), 7.79 (d, J=7.6 Hz, 1H), 7.39 (t, J=7.8 Hz, 1H), 7.11 (t, J=7.6 Hz, 1H) ppm $^{19}$F-NMR (188 MHz, CDCl$_3$) δ −42.3 (s) ppm.

Preparation of (trifluoromethyl)(2-(2-phenylethynyl)phenyl)sulfide

[Chemical formula 16]

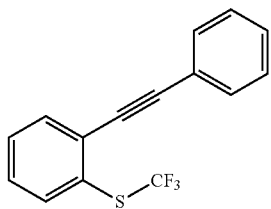

A suspension of PdCl$_2$PPH$_3$ (0.027 g, 0.063 mmol) and copper iodide (0.0035 g, 0.018 mmol) in 3 ml of triethylamine was charged into a 50-ml eggplant flask equipped with a stirrer. To this suspension, a solution of (trifluoromethyl)(2-iodophenyl)sulfide (0.57 g, 1.9 mmol) prepared in Example 1 and phenylacetylene (0.23 g, 2.2 mmol) in 2 ml of triethylamine was added dropwise at room temperature, and the mixture was stirred overnight. After completion of the reaction, a solvent was removed, water was added to the obtained residue, and the mixture was extracted three times with ether. The obtained organic layers was collected and washed with water, dried over anhydrous sodium sulfate, and concentrated to obtain a crude product. The obtained crude product was purified by silica gel column chromatography (Benzen/Hexane=20/80) to give target (trifluoromethyl)-(2-(2-phenylethynyl)phenyl)sulfide (0.5 g, 96%).

$^1$H-NMR (200 MHz, CDCl$_3$) δ 7.74-7.32 (m, 9H) ppm.
$^{19}$F-NMR (188 MHz, CDCl$_3$) δ −41.9 (s) ppm.

Preparation of S-(trifluoromethyl)-2-phenylbenzo[b]thiophenium trifluoromethanesulfonate

[Chemical formula 17]

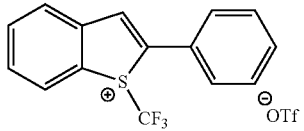

A solution of (trifluoromethyl)-(2-(2-phenylethynyl)phenyl)sulfide (1.5 g, 5.4 mmol) prepared in Example 2 in 10 ml of methylene chloride was charged into a 50-ml eggplant flask equipped with a stirrer, and cooled to −80° C. Then, trifluoromethanesulfonic acid (1.62 g, 10.8 mmol) was added dropwise to the solution, and the solution was gradually heated to room temperature, and stirred overnight. After completion of the reaction, a solvent was removed, ether was added to the obtained residue to cause solidification, and the solidified product was filtered and washed with ether. The obtained crude product was dissolved in acetonitrile, and ether was added to the solution to cause crystallization to obtain target S-(trifluoromethyl)-2-phenylbenzo[b]thiophenium trifluoromethanesulfonate (1.8 g, 80%).

$^1$H-NMR (200 MHz, Acetone-d$_6$) δ 8.77-8.71 (m, 2H), 8.28-7.96 (m, 5H), 7.74-7.68 (m, 3H) ppm.

$^{19}$F-NMR (188 MHz, Acetone-d$_6$) δ −51.3 (s, 3H), −78.2 (s, H) ppm.

$^{13}$C-NMR (150 MHz, Acetone-d$_6$) δ 146.2, 140.1, 137.2, 136.1, 132.5, 132.4, 130.6, 130.5, 129.2, 128.5, 128.1, 124.6, 123.9 (q, J=328 Hz, CF$_3$), 121.9 (q, J=327, CF3) ppm.

IR (KBr) 3936, 3828, 3801, 3738, 3726, 3627, 3487, 3086, 3040, 1578, 1451, 1278, 1242, 1222, 1161, 1075, 1028, 927, 766, 693, 637 cm$^{-1}$.

MS (ESI) m/z 279 (M$^+$-CF$_3$SO$_3$).

Example 39

Preparation of 2-(3-methyl-3-(trifluoromethyl)-(7-chloroindannylidene))malononitrile 2-(3-methyl-3-(trifluoromethyl)-(7-chloroindaylidene)malononitrile (yield: 58%) was obtained by using the same instruments as in Example 37 and performing the same operation as in Example 37 except that 2-phenyl-1-trifluoromethylbenzo[b]thiophenium triflate was used instead of 2-cyclopropyl-1-trifluoromethylbenzo[b]thiophenium triflate.

Example 40

Preparation of 2-(3-bis(trifluoromethyl)-indaylidene)malononitrile

[Chemical formula 18]

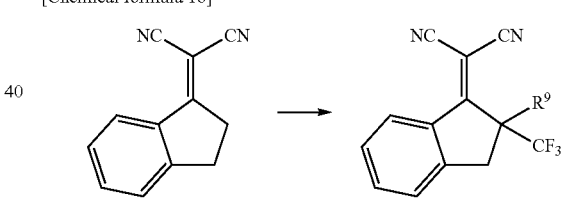

Target 2-(3-bis(trifluoromethyl)-indaylidene)malononitrile (yield: 70%) was obtained by using the same instruments as in Example 34 and performing the same operation as in Example 34 except that 2-indaylidenemalononitrile was used as a raw material, and 2.0 mol of base $^1$P was used.

Example 41

Preparation of Benzyl 2-methyl-2-(trifluoromethyl)-3-oxopentanoate

[Chemical formula 19]

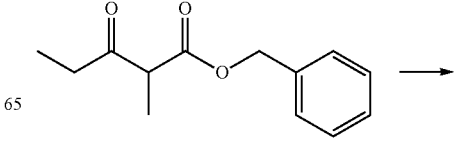

-continued

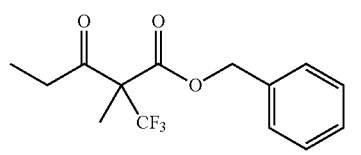

5

Methyl benzyl 2-methyl-3-oxopentanoate (22.0 mg, 0.1 mol), acetonitrile (1 ml), and tert-butylamino-tri(pyrolodino)phosphorane (37.5 mg, 0.12 mmol) were charged into a 5-ml round-bottomed flask equipped with a stirrer, and the mixture was subjected to reaction at room temperature for 15 minutes, cooled to −43 to −45° C., and stirred for 5 minutes. To this mixture, a solution of 2-cyclopropyl-1-trifluoromethylbenzo[b]thiophenyl triflate (58.8 mg, 0.15 mmol) prepared in Example 2 in acetonitrile (1 ml) was added dropwise over 15 minutes, and the mixture was stirred at the same temperature for 15 minutes. After completion of the reaction, the temperature was raised to room temperature, and a solvent was distilled off. The obtained residue was purified by silica gel column chromatography (benzene) to obtain target benzyl 2-methyl-2-(trifluoromethyl)-3-oxopentanoate (18.3 mg, yield: 80%) as an oil.

Example 42

Preparation of Benzyl 2-methyl-2-(trifluoromethyl)-3-oxopentanoate

Benzyl 2-methyl-2-(trifluoromethyl)-3-oxopentanoate (14.2 mg, yield: 62%) was obtained by using the same instruments as in Example 39 and performing the same operation as in Example 39 except that 2-phenyl-1-trifluoromethylbenzo[b]thiophenium triflate was used instead of 2-cyclopropyl-1-trifluoromethylbenzo[b]thiophenium triflate.

Comparative Example 1

Benzyl 2-methyl-2-(trifluoromethyl)-3-oxopentanoate was obtained by using the same instruments as in Example 39 and performing the same operation as in Example 39 except that (S)-trifluoromethylthiophenium 2-sulfonate instead of 2-cyclopropyl-1-trifluoromethylbenzo[b]thiophenium triflate. The yield was as low as 14.0 mg and 59%.

INDUSTRIAL APPLICABILITY

The trifluoromethylthiophenium derivative salt of the present invention represented by the general formula (1) is an excellent trifluoromethylating agent and a trifluoromethyl-containing compound is a useful compound used as synthetic intermediates for pharmaceuticals and agrochemicals.

The invention claimed is:

1. An S-(trifluoromethyl)-benzo[b]thiophenium salt represented by formula (1),

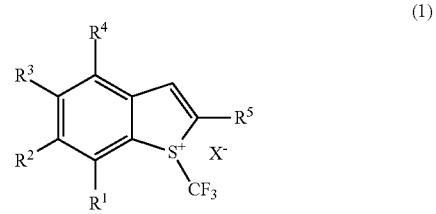

(1)

wherein $R^1$, $R^2$, $R^3$, and $R^4$ each independently represent a hydrogen atom, a methyl group, an ethyl group, a linear, branched, or cyclic alkyl group having 3 to 10 carbon atoms, a methoxy group, an ethoxy group, a linear, branched, or cyclic alkyloxy group having 3 to 10 carbon atoms, a fluorine atom, a chlorine atom, a bromine atom, a nitro group, or a cyano group, $R^5$ is a methyl group, an ethyl group, a linear, branched, or cyclic alkyl group having 3 to 10 carbon atoms, a phenyl group, or a substituted phenyl group, and $X^-$ represents an anion.

2. The S-(trifluoromethyl)-benzo[b]thiophenium salt according to claim 1, wherein $R^1$, $R^2$, $R^3$, and $R^4$ are all hydrogen atoms, $R^5$ is a cyclic alkyl group having 3 to 7 carbon atoms, and $X^-$ is a trifluoromethanesulfonate ion or a tetrafluoroborate ion.

3. The S-(trifluoromethyl)-benzo[b]thiophenium salt according to claim 1, wherein $R^5$ is a cyclopropyl group.

4. A method for producing the S-(trifluoromethyl)-benzo[b]thiophenium salt represented by formula (1) according to claim 1, comprising:

reacting a (trifluoromethyl)-(2-ethynyl)phenyl sulfide represented by formula (2),

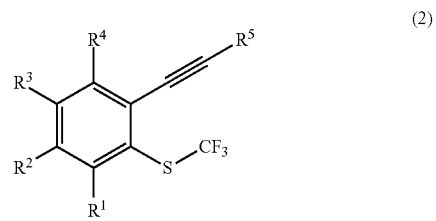

(2)

wherein $R^1$, $R^2$, $R^3$, and $R^4$ each independently represent a hydrogen atom, a methyl group, an ethyl group, a linear, branched, or cyclic alkyl group having 3 to 10 carbon atoms, a methoxy group, an ethoxy group, a linear, branched, or cyclic alkyloxy group having 3 to 10 carbon atoms, a fluorine atom, a chlorine atom, a bromine atom, a nitro group, or a cyano group, and $R^5$ is a methyl group, an ethyl group, a linear, branched, or cyclic alkyl group having 3 to 10 carbon atoms, a phenyl group, or a substituted phenyl group, with an acid.

5. A method for producing the S-(trifluoromethyl)-benzo[b]thiophenium salt represented by formula (1) according to claim 2, comprising:

reacting a (trifluoromethyl)-(2-ethynyl)phenyl sulfide represented by formula (2),

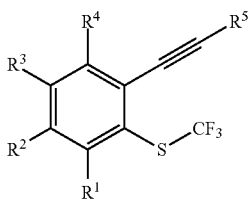

(2)

wherein $R^1$, $R^2$, $R^3$, and $R^4$ are all hydrogen atoms, and $R^5$ is a cyclic alkyl group having 3 to 7 carbon atoms,
with an acid.

6. A method for producing the S-(trifluoromethyl)-benzo[b]thiophenium salt represented by formula (1) according to claim 3, comprising:
reacting a (trifluoromethyl)-(2-ethynyl)phenyl sulfide represented by formula (2),

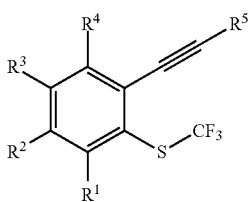

(2)

wherein $R^1$, $R^2$, $R^3$, and $R^4$ each independently represent a hydrogen atom, a methyl group, an ethyl group, a linear, branched, or cyclic alkyl group having 3 to 10 carbon atoms, a methoxy group, an ethoxy group, a linear, branched, or cyclic alkyloxy group having 3 to 10 carbon atoms, a fluorine atom, a chlorine atom, a bromine atom, a nitro group, or a cyano group, and $R^5$ is a cyclopropyl group,
with an acid.

7. The S-(trifluoromethyl)-benzo[b]thiophenium salt according to claim 2, wherein $R^5$ is a cyclopropyl group.

8. A method for producing the S-(trifluoromethyl)-benzo[b]thiophenium salt represented by formula (1) according to claim 7, comprising:
reacting a (trifluoromethyl)-(2-ethynyl)phenyl sulfide represented by formula (2),

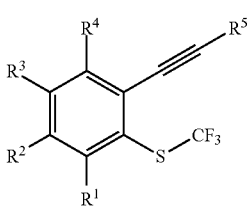

(2)

wherein $R^1$, $R^2$, $R^3$, and $R^4$ all hydrogen atoms, and $R^5$ is a cyclopropyl group,
with an acid.

9. A method for producing the S-(trifluoromethyl)-benzo[b]thiophenium salt represented by formula (1) according to claim 3, comprising:
reacting a (trifluoromethyl)-(2-ethynyl)phenyl sulfide represented by formula (2),

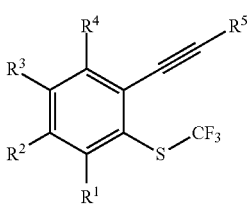

(2)

wherein $R^1$, $R^2$, $R^3$, and $R^4$ are all hydrogen atoms, and $R^5$ is a cyclopropyl group,
with an acid.

* * * * *